(12) United States Patent
Nakamura et al.

(10) Patent No.: US 10,384,008 B2
(45) Date of Patent: Aug. 20, 2019

(54) SYRINGE WITH NEEDLE, PREFILLED SYRINGE, AND MEDICAL LIQUID ADMINISTRATION TOOL USING THE SAME

(71) Applicant: TERUMO KABUSHIKI KAISHA, Shibuya-ku, Tokyo (JP)

(72) Inventors: Koji Nakamura, Kanagawa (JP); Tetsuya Oyauchi, Yamanashi (JP); Ayumi Kumagai, Gifu (JP); Takeshi Akiyama, Yamanashi (JP); Shigeru Tamatsukuri, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 148 days.

(21) Appl. No.: 15/145,259

(22) Filed: May 3, 2016

(65) Prior Publication Data

US 2016/0243305 A1    Aug. 25, 2016

Related U.S. Application Data

(63) Continuation of application No. PCT/JP2014/076525, filed on Oct. 3, 2014.

(30) Foreign Application Priority Data

Nov. 3, 2013   (JP) .................................. 2013-228867

(51) Int. Cl.
*A61M 5/20* (2006.01)
*A61M 5/31* (2006.01)
(Continued)

(52) U.S. Cl.
CPC ........ *A61M 5/2033* (2013.01); *A61M 5/3134* (2013.01); *A61M 5/31513* (2013.01);
(Continued)

(58) Field of Classification Search
CPC .............. A61M 5/2033; A61M 5/3134; A61M 5/31513; A61M 5/3286
(Continued)

(56) References Cited

U.S. PATENT DOCUMENTS 5,665,071 A * 9/1997 Wyrick ................. A61M 5/002
                                                              604/131
2004/0078008 A1* 4/2004 Ueda ..................... A61M 5/329
                                                              604/272

(Continued)

FOREIGN PATENT DOCUMENTS

JP       2004-041391 A    2/2004
WO    WO 2009/084646 A   7/2009
(Continued)

OTHER PUBLICATIONS

International Search Report (PCT/ISA/210) dated Dec. 2, 2014, by the Japanese Patent Office as the International Searching Authority for International Application No. PCT/JP2014/076525.

(Continued)

*Primary Examiner* — Phillip A Gray
(74) *Attorney, Agent, or Firm* — Buchanan Ingersoll & Rooney PC

(57) ABSTRACT

A syringe is disclosed, which includes a needle having an outer cylinder including an outer cylinder body part and a needle fixing part provided at a distal end part of the outer cylinder body part; an injection needle 6 having a puncturing needle tip at a distal end and fixed to the needle fixing part; and a gasket housed in the outer cylinder. The injection needle is such a tapered part holding injection needle that a puncturing time piercing part having a needle tip has an outer diameter of 0.42 mm or less and has a thickness of 0.1 mm or less, or the injection needle is such a small diameter thin injection needle as to have a thickness of 0.04 mm or less. The gasket includes a gasket body and a soft coating (Continued)

provided on a portion that comes into contact with the inner surface of the outer cylinder.

20 Claims, 14 Drawing Sheets

(51) Int. Cl.
- *A61M 5/32* (2006.01)
- *A61M 5/315* (2006.01)
- *A61M 5/34* (2006.01)

(52) U.S. Cl.
CPC .......... *A61M 5/329* (2013.01); *A61M 5/3286* (2013.01); *A61M 5/343* (2013.01); *A61M 5/3202* (2013.01); *A61M 5/326* (2013.01); *A61M 2005/2013* (2013.01); *A61M 2202/07* (2013.01); *A61M 2205/0238* (2013.01)

(58) Field of Classification Search
USPC ........................................................ 604/222
See application file for complete search history.

(56) References Cited

U.S. PATENT DOCUMENTS

| | | |
|---|---|---|
| 2005/0234386 A1 | 10/2005 | Nishikawa et al. |
| 2014/0296797 A1 | 10/2014 | Iwase et al. |
| 2015/0133873 A1 | 5/2015 | Horiuchi et al. |

FOREIGN PATENT DOCUMENTS

| | | |
|---|---|---|
| WO | WO 2013/027799 A1 | 2/2013 |
| WO | WO 2013/065814 A1 | 5/2013 |

OTHER PUBLICATIONS

Written Opinion (PCT/ISA/237) dated Dec. 2, 2014, by the Japanese Patent Office as the International Searching Authority for International Application No. PCT/JP2014/076525.

* cited by examiner

SYRINGE WITH NEEDLE, PREFILLED SYRINGE, AND MEDICAL LIQUID ADMINISTRATION TOOL USING THE SAME

CROSS-REFERENCES TO RELATED APPLICATIONS

This application is a continuation of International Application No. PCT/JP2014/076525 filed on Oct. 3, 2014, and claims priority to Japanese Application No. 2013-228867 filed on Nov. 3, 2013, the entire content of both of which is incorporated herein by reference.

TECHNICAL FIELD

The present disclosure relates to a syringe with needle, a prefilled syringe, and a medical liquid administration tool suitable for injecting a high-viscosity drug.

BACKGROUND DISCUSSION

As a syringe for administering a small amount of drug such as a protein preparation, an antibody preparation, a hyaluronic acid, and insulin, such a syringe can include a thin diameter puncture needle that is fixed to a distal end part of an outer cylinder. In many cases, a high-viscosity drug is used as a drug. When such a high-viscosity drug is administered, an administering operation might not be easy, since a small diameter puncture needle has high flow resistance. Although silicone oil is sometimes applied to an inner surface of an outer cylinder as a sliding property, such a lubricant might cause aggregation or denaturation of a drug due to an interaction with a placed drug.

Therefore, a lubricant is preferably not used in a syringe. However, since a sliding property in an outer cylinder of a gasket can be deteriorated in such a syringe, an administering operation becomes difficult. Furthermore, by having such a sliding property, a risk of occurrence of a secondary medical accident is increased due to a syringe that is broken at the time of administration. Therefore, a means to lower a sliding resistance value without using a lubricant is desired in consideration of drug stability and safety during administration.

In this context, a gasket has been proposed in WO 2009/084646 A1 by the present applicant. The present applicant has also proposed JP 2004-041391 A.

The gasket of WO 2009/084646 A1 has a relatively good sliding property. Owing to an injection needle of JP 2004-041391 A, an injection can be performed without hurting or damaging a patient, and further without causing a patient to feel fearful or anxious. The injection needle of JP 2004-041391 A is relatively suitable since it can reduce channel resistance of the entire injection needle when a drug solution is injected into a living body.

As a syringe with needle, however, a syringe with needle capable of administering a drug solution having a higher concentration at low injection resistance and with low gasket pressing force is required.

SUMMARY OF INVENTION

In this regard, the present disclosure provides a syringe with needle, a prefilled syringe, and a medical liquid administration tool capable of administering a drug solution having a high concentration or a high viscosity at low injection resistance and with low gasket pressing force.

A syringe is disclosed with a needle including an outer cylinder including an outer cylinder body part and a needle fixing part provided at a distal end part of the outer cylinder body part; an injection needle having a puncturing needle tip at a distal end, a proximal end part of the injection needle being fixed to the needle fixing part of the outer cylinder; and a gasket housed in the outer cylinder and capable of sliding within the outer cylinder in a liquid-tight state, wherein the injection needle is such a tapered part holding injection needle that a puncturing time piercing part having the puncturing needle tip has an outer diameter of 0.42 mm or less and has a thickness of 0.1 mm or less, the tapered part holding injection needle having a proximal end with a greater outer diameter than the puncturing time piercing part, or the injection needle is such a small diameter ultrathin injection needle that a puncturing time piercing part having the puncturing needle tip has an outer diameter of 0.42 mm or less and has a thickness of 0.04 mm or less, the small diameter ultrathin injection needle extending from a distal end to a proximal end with substantially the same outer diameter, and the gasket includes a gasket body made of an elastic body and a soft coating provided on at least a portion that comes into contact with the inner surface of the outer cylinder, the soft coating having a liquid-tight sliding property with respect to the inner surface of the outer cylinder.

In accordance with an exemplary embodiment, a lubricant is not applied to an inner surface of the outer cylinder.

DESCRIPTION OF EMBODIMENTS

Figure 1:
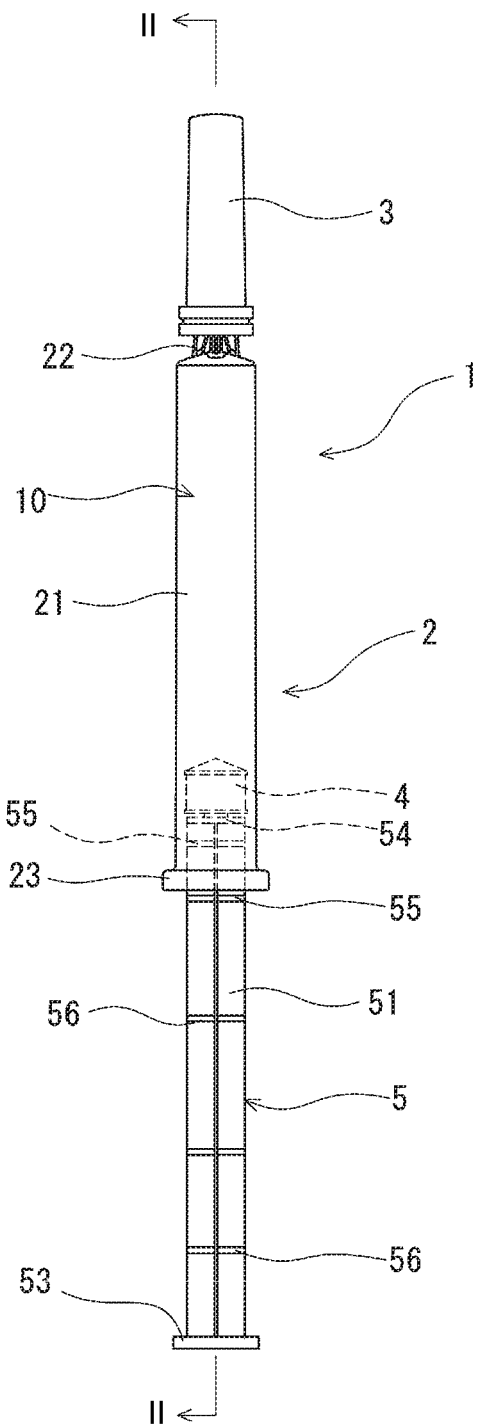
FIG. 1 is a front view of a prefilled syringe in which a syringe with needle according to an example of the present disclosure is used.

A syringe with needle, a prefilled syringe, and a medical liquid administration tool using the same according to the present disclosure will be described using an embodiment illustrated in the drawings.

The prefilled syringe 1 according to the present disclosure can include a syringe with needle 2, a seal cap 3, and a medical liquid 7. The seal cap 3 seals a distal end part of an injection needle 6 of the syringe with needle. The syringe with needle 2 is filled with the medical liquid 7.

The syringe with needle 2 according to the present disclosure has an outer cylinder 10, the injection needle 6, and a gasket 4. The outer cylinder 10 can include an outer cylinder body part 21 and a needle fixing part 22 provided at a distal end part of the outer cylinder body part 21. The injection needle 6 has a puncturing needle tip 61 at the distal end, and a proximal end part 67 of the injection needle 6 is fixed to the needle fixing part 22 of the outer cylinder 10. The gasket 4 is housed in the outer cylinder 10 and capable of sliding within the outer cylinder 10 in a liquid-tight state. The injection needle 6 is such a tapered part holding injection needle that a puncturing time piercing part 65 having the puncturing needle tip has an outer diameter of 0.42 mm or less (27 G or less) and has a thickness of 0.1 mm or less, the tapered part holding injection needle having a proximal end with a greater outer diameter than the puncturing time piercing part. Alternatively, the injection needle 6 is such a small diameter ultrathin injection needle that a puncturing time piercing part having the puncturing needle tip has an outer diameter of 0.42 mm or less and has a thickness of 0.04 mm or less, the small diameter ultrathin injection needle extending from a distal end to a proximal end with substantially the same outer diameter. In accordance with an exemplary embodiment, a lubricant is not applied to an inner surface of the outer cylinder 10. The gasket 4 can include a gasket body 41 and a soft coating 42. The gasket body 41 can be made of an elastic body. The soft coating 42 is provided on at least a portion that comes into contact with the inner surface of the outer cylinder 10, and has an adhesive property (difficult peeling property) to the gasket body 41 and a liquid-tight sliding property with respect to the inner surface of the outer cylinder 10.

As illustrated in FIGS. 1 to 6, the syringe with needle 2 according to the present example can include the outer cylinder 10, the injection needle 6, the seal cap 3 mounted on the outer cylinder 10 so as to seal the needle tip 61 of the injection needle 6, the gasket 4 housed in the outer cylinder 10, and a plunger 5 attached to the gasket 4 or to be attached to the gasket 4 at the point of use.

The outer cylinder 10 can include the outer cylinder body part 21, the injection needle attaching part 22 provided at the distal end part of the outer cylinder body part 21, and a flange 23 provided at the proximal end of the outer cylinder body part 21. In accordance with an exemplary embodiment, the outer cylinder 10 is used in such a manner that a lubricant is not applied to the inner surface.

The syringe with needle according to the present example is configured such that the gasket 4 within the outer cylinder 10 has an initial sliding resistance value around or equal to or less than a maximum value of a dynamic sliding resistance value, resulting in a relatively good initial sliding of the gasket.

In accordance with an exemplary embodiment, the outer cylinder 10 is transparent or translucent. The outer cylinder body part 21 is a substantially cylindrical portion that houses the gasket 4 such that the gasket 4 is slidable in a liquid-tight manner. The injection needle attaching part 22 protrudes forward beyond the distal end part of the outer cylinder body part (in the present example, a shoulder part that is reduced in diameter toward a distal end direction formed at a distal end of a cylindrical body part). The injection needle attaching part 22 can also be formed in a hollow cylindrical shape, a diameter of which is smaller than that of the outer cylinder body part. The injection needle attaching part 22 has, as illustrated in FIGS. 2 to 6, an annular head part 24, a short tapered reduced diameter part 25, and a coupling part 27. The annular head part 24 is provided at a distal end of the injection needle attaching part 22. The tapered reduced diameter part 25 is provided at a proximal end of the annular head part 24 and reduced in diameter toward a proximal end direction. The coupling part 27 couples a proximal end part of the tapered reduced diameter part 25 to the distal end part of the outer cylinder body part 21. An annular recessed part is formed by the tapered reduced diameter part 25.

In the annular head part 24, a recess 26 and a hollow conical part are formed. The recess 26 is recessed from a distal end surface toward a proximal end side. The conical part is positioned within the recess 26 and has an apex at a distal end side. In an outer surface of the coupling part 27, a plurality of grooves extending in an axial direction of the outer cylinder 10 is formed. The annular recessed part may not be a tapered shape but may be such a shape as to be simply reduced in diameter so that a step is formed between the annular recessed part and the proximal end of the annular head part 24. The coupling part 27 also has a function to enhance fixing strength of a needle. However, in a case where strength can be obtained even if the coupling part 27 is removed, the proximal end part of the annular recessed part (tapered reduced diameter part 25) may be directly connected to the distal end part of the outer cylinder body part 21. The annular head part 24 may be a hollow columnar shape (cylindrical shape) from which the recess 26 and the conical part are removed.

Glass or plastic can be used as a forming material for the outer cylinder 10, and plastic is preferably used. Examples of the plastic include, for example: polyesters such as polypropylene, polyethylene, polystyrene, polyamides, polycarbonates, polyvinyl chloride, poly(4-methylpentene-1), acrylic resins, an acrylonitrile-butadiene-styrene copolymer, and polyethylene terephthalate; and various resins such as a cyclic olefin polymer and a cyclic olefin copolymer. Among them, resins such as polypropylene, a cyclic olefin polymer, and a cyclic olefin copolymer are preferable since they are easy to mold, have excellent transparency, do not affect drugs, and have heat resistant properties.

The injection needle 6 has the puncturing needle tip 61 at the distal end. The proximal end part of the injection needle 6 is inserted into the hollow part of the injection needle attaching part 22, and an inner part 60 of the injection needle 6 is in communication with an internal space 20 of the outer cylinder 10.

In the syringe with needle 2 according to the present example, the injection needle 6 is undetachably fixed to the outer cylinder 10. As a method of fixing the injection needle 6 to the outer cylinder 10, for example, the injection needle 6 may be inserted into the hollow part of the injection needle attaching part 22 of the outer cylinder 10 that has been molded in advance, and fixed to the injection needle attaching part 22 by means of an adhesive, or heat welding.

Alternatively, the injection needle 6 may be directly inserted and molded into the outer cylinder 10 to be fixed. In the insert molding, when the outer cylinder 10 is molded, the injection needle attaching part 22 is formed in a cylindrical shape (hollow shape) into which the injection needle 6 is inserted, and the injection needle 6 is configured such that the proximal end part thereof is inserted and fixed into the hollow part of the injection needle attaching part 22.

Furthermore, the injection needle 6 may be fixed to the outer cylinder 10 by means of fusion (for example, heat fusion, ultrasonic fusion, laser fusion, induction heating fusion) using a thermoplastic resin cylindrical member. In this case, an outer cylinder having a hollow distal end part having an inner cavity part capable of housing the thermoplastic resin cylindrical member is used as the outer cylinder 10. A thermoplastic resin cylindrical member having a communication hole capable of housing the proximal end part of the injection needle is used as the thermoplastic resin cylindrical member. The thermoplastic resin cylindrical member into which the proximal end part of the injection needle has been inserted is inserted into the hollow distal end part of the outer cylinder, and the thermoplastic resin cylindrical member is directly or indirectly heated and melted, whereby the injection needle is fixed to the outer cylinder via the thermoplastic resin cylindrical member.

A hollow injection needle having the puncturing needle tip 61 at a distal end is used as the injection needle 6. A forming material for the injection needle 6 is generally metal. Stainless steel is a suitable metal. An inner surface of the injection needle 6 preferably has an average roughness (Ra), for example, of less than 0.3 μm. Owing to such a smooth inner surface, flow resistance of a drug can be reduced. In particular, the average roughness (Ra) of the inner surface, for example, is preferably less than 0.2 μm.

The syringe with needle 2 according to the present example can employ such a tapered part holding injection needle that the puncturing time piercing part 65 having the puncturing needle tip has an outer diameter, for example, of 0.42 mm or less (27 G or less) and has a thickness, for example, of 0.1 mm or less, the tapered part holding injection needle having a proximal end 62 with a greater outer diameter than the puncturing time piercing part 65. This injection needle corresponds to a small diameter thin injection needle. The above-mentioned type of the piercing part 65 having the needle tip gives less pain to a patient at the time of puncture and has low puncture resistance. Furthermore, the injection needle has a thin diameter but also has a thin thickness, thereby having a sufficient inner diameter, resulting in a relatively good drug flow.

The tapered part holding injection needle 6 is provided with the proximal end 62 having a greater diameter than the puncturing time piercing part 65. The outer diameter of the proximal end 62 is preferably greater than the outer diameter of the puncturing time piercing part 65, for example, by 0.05 mm or more. As mentioned above, when the injection needle 6 has the proximal end part thicker than the distal end part, stiffness is increased to suppress bending or the like at the time of puncture. In particular, the outer diameter of the proximal end 62 of the injection needle 6 is preferably greater than the outer diameter of the puncturing time piercing part 65, for example, by 0.15 mm or more.

Figure 5:
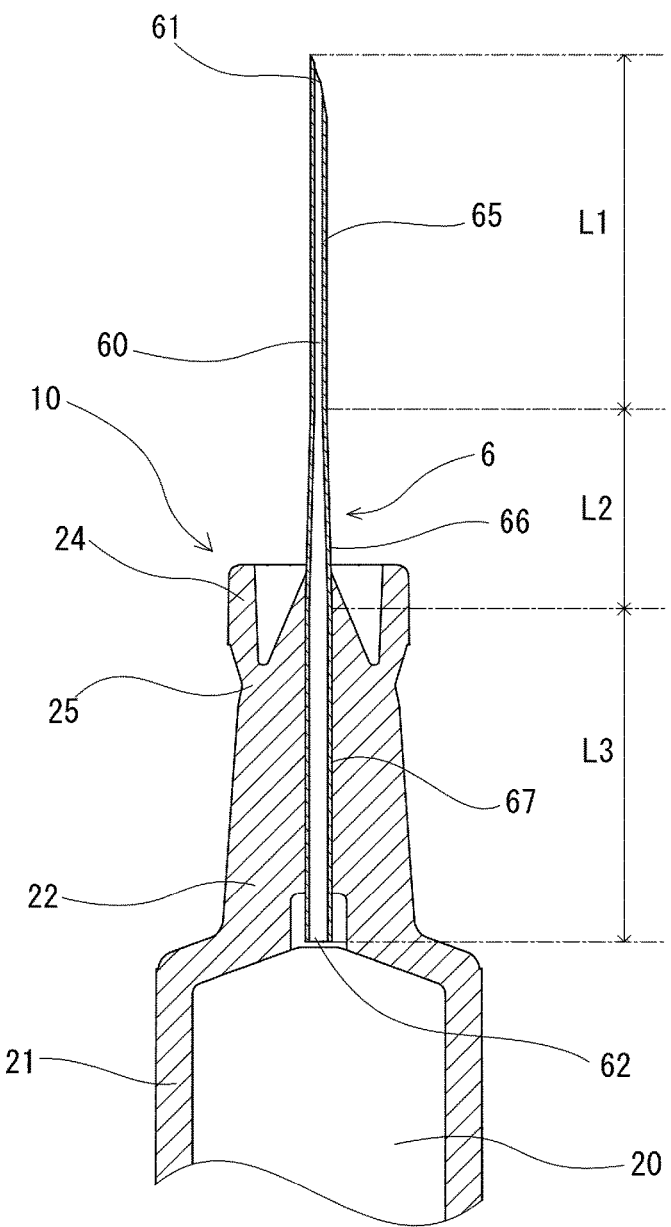
FIG. 5 is an enlarged cross-sectional view of a distal end part of the outer cylinder illustrated in FIG. 3.

The tapered part holding injection needle 6 used in the syringe with needle 2 according to the present example can include, as illustrated in FIG. 5, the puncturing time piercing part 65 and a tapered part 66. The puncturing time piercing part 65 extends by a predetermined length with substantially the same outer diameter. The tapered part 66 is expanded in diameter in a tapered manner from a proximal end toward a rear end of the puncturing time piercing part 65. A portion including the tapered part 66 (specifically, a proximal end part of the tapered part 66) is fixed to the injection needle attaching part 22. Therefore, the injection needle 6 is hardly detached from the injection needle attaching part 22. In the syringe with needle in which the above-mentioned tapered part holding injection needle is used as the injection needle, the injection needle is directly inserted and molded into the outer cylinder, whereby the syringe with needle that effectively prevents the needle from being detached can be manufactured using facilities and members similar to those of a straight injection needle.

Furthermore, the injection needle 6 according to the present example can include, as illustrated in FIG. 5, the proximal end part 67 extending by a predetermined length with substantially the same outer diameter from a proximal end toward a rear end of the tapered part 66. Therefore, the injection needle can be fixed to the injection needle attaching part with a sufficient contact area, resulting in a stable fixed state.

The injection needle 6 may be fixed to the outer cylinder 10 by means of laser welding. The injection needle fixing part 22 of the outer cylinder 10 can include an insertion hole (through passage) having an inner diameter somewhat greater than a maximum outer diameter in the proximal end part of the injection needle 6. The through passage of the outer cylinder 10 before the attachment of the injection needle extends with substantially the same outer diameter. The injection needle may be fixed to the outer cylinder in such a manner that after the proximal end part of the tapered part 66 of the injection needle 6 is inserted into a lower end part of the insertion hole, the proximal end part of the injection needle 6 is irradiated with a laser to cause the injection needle to generate heat, whereby an inner surface of the insertion hole is melted. The insertion hole (through passage) may be reduced in diameter toward a distal end. In this case, the degree of diameter reduction is preferably substantially the same as the degree of diameter reduction in the proximal end part of the tapered part of the injection needle. In this case, the distal end of the injection needle is inserted from a proximal end side of the injection needle fixing part 22 of the outer cylinder 10.

Furthermore, the injection needle 6 may be fixed to the injection needle fixing part of the outer cylinder 10 through an inner cylindrical body (not illustrated). Such an inner cylindrical body is used as the inner cylindrical body as to have an outer surface shape capable of being inserted into the injection needle fixing part of the outer cylinder, and can include, at the inside, an insertion hole into which the proximal end part of the tapered part 66 of the injection needle 6 can be inserted. The insertion hole of the inner cylindrical body preferably can include a reduced diameter inner surface that reduces an inner diameter of the insertion hole. The reduced diameter inner surface is preferably formed on such a tapered surface (conical surface) that an inner diameter of the insertion hole is gradually decreased from a proximal end side toward a distal end side of the insertion hole. A taper angle of the reduced diameter inner surface is preferably substantially the same angle as a taper angle of a reduced diameter outer surface of the injection needle. A tapered part of the reduced diameter outer surface of the injection needle of the injection needle inserted into the insertion hole abuts on the reduced diameter inner surface of the insertion hole.

As a result, the injection needle is locked with respect to the inner cylindrical body so as to be prevented from moving in a removal direction, that is, moving toward a distal end side. It is preferable that the injection needle fixing part of the outer cylinder is formed on such a tapered surface (conical surface) that the inner diameter of the injection needle fixing part is gradually decreased from the proximal end side toward the distal end side, and the outer surface shape of the inner cylindrical body capable of being inserted into the injection needle fixing part of the outer cylinder is formed on such a tapered part that an outer diameter of the inner cylindrical body is gradually increased from a proximal end side toward a distal end side. It is also preferable that a taper angle of the injection needle fixing part is substantially the same angle as a taper angle of the outer surface shape of the inner cylindrical body. In the syringe with needle of the type having this inner cylindrical body, the injection needle and the inner cylindrical body are fixed to the outer cylinder in such a manner that after the inner cylindrical body holding the injection needle is inserted into an opening part of the distal end part of the outer cylinder, the proximal end part of the injection needle is irradiated with a laser to cause the injection needle to generate heat, whereby the inner cylindrical body and a portion of the distal end part of the outer cylinder abutting on the inner cylindrical body are melted.

The outer diameter of the piercing part 65 is, for example, equal to or less than 0.42 mm, and preferably, for example, equal to or less than 0.35 mm. An inner diameter of the piercing part 65 is preferably equal to or greater than 0.05 mm in terms of ensuring a flow rate. The inner diameter is preferably, for example, equal to or less than 0.34 mm since the outer diameter of the piercing part does not become too large. The inner diameter is particularly preferably, for example, 0.1 mm to 0.3 mm. A thickness of the injection needle 6 at the piercing part 65 is preferably, for example, 0.04 mm to 0.08 mm, and particularly preferably, for example, 0.04 mm to 0.06 mm. A length L1 (FIG. 5) of the piercing part 65 is preferably, for example, 4.0 mm to 12.0 mm, and particularly preferably, for example, 5.0 mm to 10.0 mm. The piercing part 65 may be any of such a piercing part that the entire piercing part pierces a living body at the time of puncture and such a piercing part that only a distal end side portion pierces a living body at the time of puncture. Furthermore, a distal end part of the tapered part 66, which will be described later, may also pierce a living body at the time of puncture.

In accordance with an exemplary embodiment, an outer diameter of the rear end of the tapered part 66 is preferably greater than the outer diameter of the piercing part 65, for example, by 0.05 mm or more, specifically equal to or greater than 0.40 mm, and preferably equal to or greater than 0.55 mm. An inner diameter of the proximal end of the tapered part 66 is preferably, for example, equal to or greater than 0.30 mm, and particularly preferably equal to or greater than 0.43 mm. A thickness of the injection needle 6 at the tapered part 66 is preferably, for example, 0.04 mm to 0.08 mm, and particularly preferably 0.04 mm to 0.06 mm. A length L2 (FIG. 5) of the tapered part 66 is preferably, for example, 1.0 mm to 10.0 mm, and particularly preferably 2.0 mm to 8.0 mm.

An outer diameter of a proximal end of the proximal end part 67 is preferably, for example, greater than the outer diameter of the piercing part 65, for example, by 0.05 mm or more, specifically equal to or greater than 0.40 mm, and preferably equal to or greater than 0.55 mm. An inner diameter of the proximal end of the proximal end part 67 is preferably, for example, equal to or greater than 0.30 mm, and particularly preferably equal to or greater than 0.43 mm.

A thickness of the injection needle 6 at the proximal end part 67 is preferably, for example, 0.04 mm to 0.08 mm, and particularly preferably 0.04 mm to 0.06 mm. A length L3 (FIG. 5) of the proximal end part 67 is preferably, for example, 3.0 mm to 12.0 mm, and particularly preferably 4.0 mm to 10.0 mm.

A ratio of the distal end outer diameter to the proximal end outer diameter of the injection needle 6 is preferably, for example, 1:1.2 to 2.5, and particularly preferably 1:1.2 to 2.0. A ratio of the inner diameter of the piercing part 65 of the injection needle 6 to the inner diameter of the proximal end of the proximal end part 67 of the injection needle 6 is preferably, for example, 1:1.5 to 2.5, and particularly preferably 1:1.7 to 2.3. As disclosed above, even though the injection needle has the distal end with a thin diameter, it also has the proximal end with a relatively large inner diameter, resulting in a relatively good drug flow.

In the above-mentioned example, the injection needle 6 is configured such that the piercing part 65 and the proximal end part 67 are straight parts. However, the injection needle 6 is not limited to this example. The injection needle 6 may be configured to have a tapered part extending to the proximal end of the proximal end part 67, and further may be configured to have a tapered part extending from the distal end to the proximal end.

In accordance with an exemplary embodiment, a total length of the injection needle 6 is preferably, for example, 10.0 mm to 30.0 mm, and particularly preferably 12.0 mm to 25.0 mm.

Figure 7:
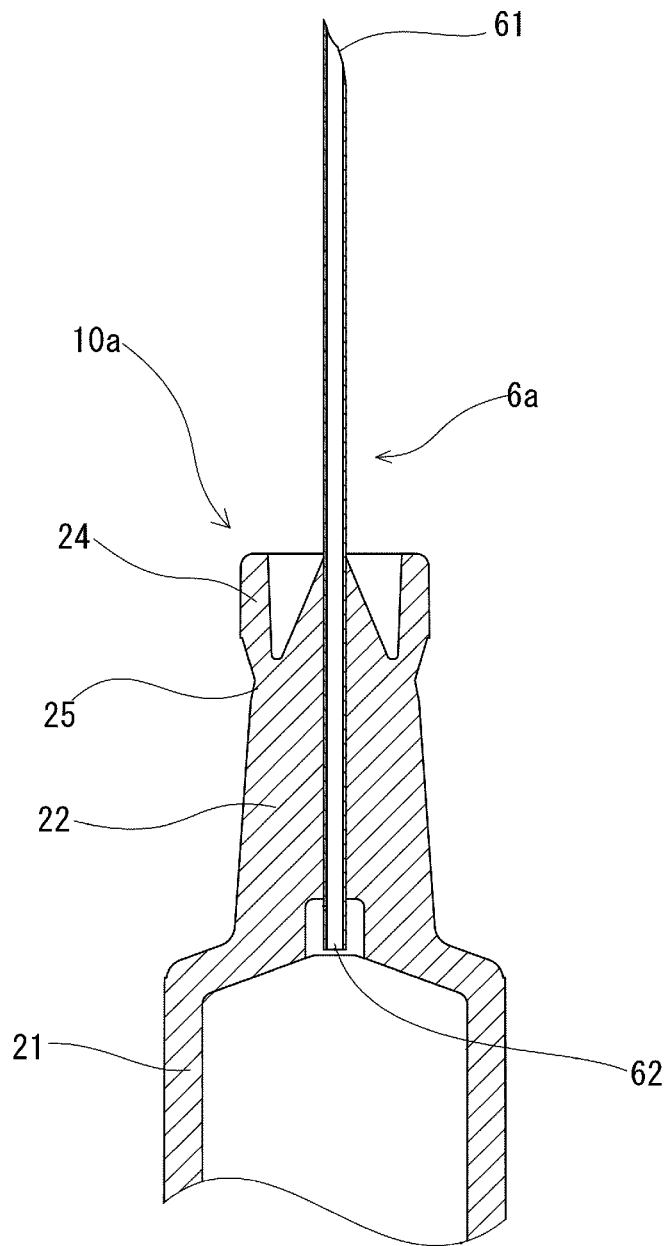
FIG. 7 is an enlarged cross-sectional view of a distal end part of an outer cylinder used in another example of the present disclosure.

Furthermore, as an outer cylinder with a needle 10a illustrated in FIG. 7, such a small diameter ultrathin injection needle may be employed as an injection needle 6a that the puncturing time piercing part 65 having the puncturing needle tip has an outer diameter of, for example, 0.42 mm or less and has a thickness of, for example, 0.04 mm or less, the small diameter ultrathin injection needle extending from the distal end to the proximal end with substantially the same outer diameter. The small diameter ultrathin injection needle 6a is a straight injection needle.

The outer diameter of the small diameter thin straight injection needle is, for example, equal to or less than 0.42 mm, and preferably equal to or less than 0.35 mm. The thickness of the injection needle 6a is preferably, for example, equal to or less than 0.04 mm, and specifically 0.02 mm to 0.04 mm. The injection needle is straight but also has a thin thickness as mentioned above, whereby a sufficient inner diameter can be ensured, resulting in a relatively good drug flow.

The gasket 4 can include the gasket body 41 and the soft coating 42 provided at a portion that is at least on an outer surface of the gasket body 41 and comes into contact with the inner surface of the outer cylinder 10. The soft coating 42 may be provided over the entire outer surface of the gasket body 41.

Figure 8:
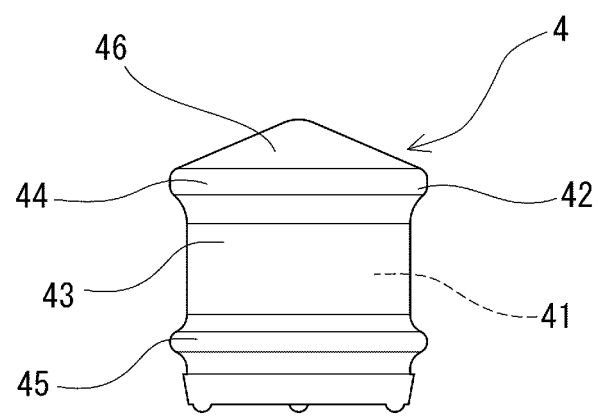
FIG. 8 is a front view of a gasket used in the syringe with needle according to the present disclosure.
Figure 9:
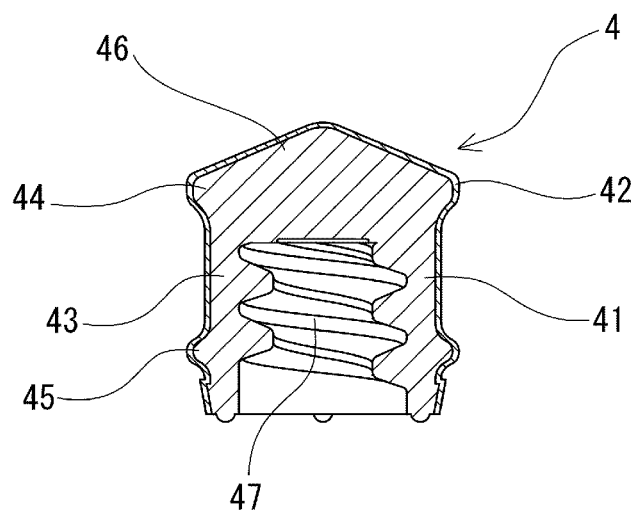
FIG. 9 is a longitudinal cross-sectional view of the gasket illustrated in FIG. 8.

The gasket body 41 can include, as illustrated in FIGS. 1, 2, 8, and 9, a body part 43, a tapered part 46, a plunger attaching part 47, a distal end side annular rib 44, and a rear end side annular rib 45. The body part 43 extends with substantially the same outer diameter. The tapered part 46 is provided on a distal end side of the body part 43 and reduced in diameter in a tapered manner toward the distal end side. The plunger attaching part 47 is provided within the body part 43 from a proximal end toward the distal end side. The distal end side annular rib 44 is provided on a side surface of a distal end part of the body part 43. The rear end side annular rib 45 is provided at a side surface of a rear end part of the body part 43. The plunger attaching part 47 is, as illustrated in FIG. 9, a substantially columnar recessed part extending within the body part 43 from the proximal end to the vicinity of the distal end part. On a side surface of the recessed part, a screw part that can be screwed with a screw part formed at a distal end part of the plunger is provided.

Since the annular ribs 44, 45 are produced somewhat larger than an inner diameter of the outer cylinder body part 21 of the outer cylinder 10, the annular ribs 44, 45 can be compressively deformed within the outer cylinder 10. Although the two annular ribs are provided in the example, a single annular rib or three or more annular ribs may be provided.

A constituent material for the gasket body 41 is preferably an elastic material. Examples of the elastic material include, but not limited to, for example: various rubber materials (in particular, vulcanized rubber materials) such as natural rubber, isoprene rubber, butyl rubber, chloroprene rubber, nitrile-butadiene rubber, styrene-butadiene rubber, and silicone rubber; styrene-based elastomers; hydrogenated styrene-based elastomers; mixtures of styrene-based elastomers and polyolefins such as polyethylene, polypropylene, polybutene, and an a-olefin copolymer; mixtures of styrene-based elastomers and oils such as liquid paraffin and process oil; and mixtures of styrene-based elastomers and powder inorganic materials such as talc, cast, and mica. Furthermore, polyvinyl chloride-based elastomers, olefin-based elastomers, polyester-based elastomers, polyamide-based elastomers, polyurethane-based elastomers, and mixtures thereof can be used as the constituent material. In particular, for example, butyl rubber is preferable as the constituent material since, for example, it has an elastic property and can be subjected to high-pressure steam sterilization. Furthermore, diene-based rubber and styrene-based elastomers are preferable since, for example, they can be subjected to γ-ray sterilization and electron beam sterilization.

The soft coating 42 is soft and has the adhesive property (difficult peeling property) to the gasket body 41 and the liquid-tight sliding property with respect to the inner surface of the outer cylinder 10. Since the gasket 4 (soft coating 42) has the liquid-tight sliding property, the gasket 4 can slide, at relatively low initial sliding resistance and dynamic sliding resistance, within the outer cylinder in such a liquid-tight state that a filling liquid does not leak out. Since the soft coating 42 has the adhesive property and the difficult peeling property to the gasket body 41, peeling and adhesion to the inner surface of the outer cylinder substantially do not occur at the time of sliding.

The soft coating 42 is only required to be provided at a portion including the distal end side annular rib 44 and the rear end side annular rib 45. Alternatively, as illustrated in FIG. 9, the soft coating 42 may be provided over the entire side surface of the outer surface and distal end surface of the gasket body 41.

The soft coating 42 may be formed by any means as long as the soft coating 42 has the above-mentioned properties and can be used as a drug contact part of a drug container. For example, the soft coating 42 can be formed by vapor deposition, laminating, and application or spraying of a coating layer forming liquid composition.

As for the vapor deposition, the soft coating 42 can be obtained by subjecting the gasket body 41 having an appropriate surface property to the vapor deposition using fluorine itself or a fluorine-containing monomer such as fluoroolefin. As for the laminating, the soft coating 42 can be obtained by laminating, as a laminate layer by means of various known laminating methods, a film having excellent smooth and flexible properties formed by a copolymer of fluoroolefin and a copolymerization component such as acrylic esters.

In a case where a coating layer forming liquid resin composition is used, and when the resin itself that forms the coating layer is a liquid, the soft coating 42 can be obtained by applying or spraying the resin as it is, and hardening the applied or sprayed resin. When the resin itself that forms the coating layer is a viscous body or a solid body such as powder, the soft coating 42 can be obtained by applying or spraying the resin suspended or dissolved in water or an organic solvent, and hardening the applied or sprayed resin. In this case, in order to improve strength of the coating layer itself and adhesive strength to the gasket body, it can be preferable to use a resin having such a plurality of functional groups as to mutually perform crosslinking after the resin is applied or sprayed, and also establish a strong bond such as a covalent bond for the gasket body.

As a forming material for the soft coating 42, a silicone-based resin having a good adhesive property to the gasket body and holding a good liquid-tight sliding property with respect to the inner surface of the outer cylinder is preferably used. In this case, a thickness of the resin soft coating 42 is preferably, for example, 1 μm to 30 μm, and particularly preferably 3 μm to 10 μm. When the thickness is, for example, equal to or greater than 1 μm, a required sliding property can be achieved. When the thickness is, for example, equal to or less than 30 μm, the elasticity of the gasket is never affected. As the silicone-based resin, any of a solvent-based resin dissolved in an organic solvent and an aqueous resin emulsified and dispersed mainly in water can be applied. In terms of an influence on a material for the gasket or an aptitude for a drug solution housing container, an aqueous resin is preferable. The soft coating 42 can be made of a resin including a material having a lower friction coefficient than the elastic material constituting the gasket body 41. The soft coating 42 is preferably formed by a solidified substance of a soft coating forming liquid substance applied to the outer surface of the gasket body 41.

The soft coating 42 is preferably made of a composition containing a reactive silicone-based resin having a terminal silanol group. The soft coating 42 is preferably made of a composition containing a silicone-based resin made of a reactive silicone condensate having a terminal silanol group, the silicone-based resin having a siloxane bond derived from a silanol group. In accordance with an exemplary embodiment, the soft coating 42 preferably does not include solid particles. The composition containing the reactive silicone-based resin is preferably a thermosetting silicone-based resin and a normal temperature setting silicone-based resin, and particularly preferably a thermosetting silicone-based resin in terms of workability.

A reactive silicone is preferably polydimethylsiloxane having a terminal silanol group. In particular, the reactive silicone preferably has silanol groups at both terminals. When the above-mentioned polysiloxane-based silicone having a terminal silanol group is used as the reactive silicone, a condensate of this reactive silicone has a siloxane bond over the entire main chain.

As the reactive silicone having the terminal silanol group, specifically, a polysiloxane-based silicone having silanol groups at both terminals such as both-terminal silanol polydimethylsiloxane, both-terminal silanol polydiphenylsiloxane, and a both-terminal silanol diphenylsiloxane-dimethylsiloxane copolymer is preferable. Although formation of the reactive silicone is not specifically limited, the above-mentioned reactive silicone siloxane compound, or polysiloxane derived from a condensate of the reactive silicone siloxane compound dispersed, emulsified, or dissolved in an aqueous medium can be used. Furthermore, a copolymer emulsion obtained by copolymerizing, as necessary, an alkoxysilyl group-containing vinyl monomer with another vinyl monomer and an emulsion obtained by compounding an organic polymer with polysiloxane can be used.

A resin composition forming the above-mentioned silicone-based resin preferably contains a second silicone-based compound, which is different from the reactive silicone-based resin having a silanol group or a siloxane bond. As the second silicone-based compound, alkylalkoxysilane, phenylalkoxysilane, alkylphenoxysilane, aminoalkylalkoxysilane, or glycidoxyalkylalkoxysilane is suitable.

Furthermore, a composition forming the above-mentioned silicone-based resin preferably contains alkylalkoxysilane or phenylalkoxysilane as the second silicone-based compound, and further preferably contains aminoalkylalkoxysilane or/and glycidoxyalkylalkoxysilane as a third silicone-based compound.

More preferably, a resin composition forming the coating layer preferably contains alkylalkoxysilane or phenylalkoxysilane as the second silicone-based compound, and further preferably contains aminoalkylalkoxysilane as the third silicone-based compound and contains glycidoxyalkylalkoxysilane as a fourth silicone-based compound.

A composition forming the above-mentioned silicone-based resin may contain the second and the third silicone-based compounds. It is preferable to select the second silicone-based resin from among alkylalkoxysilane, alkylphenoxysilane, and phenylalkoxysilane. It is preferable to use aminoalkylalkoxysilane or glycidoxyalkylalkoxysilane as the third silicone-based compound. A composition forming the coating layer may contain the second, the third, and the fourth silicone-based compounds. It is preferable to select the second silicone-based resin from among alkylalkoxysilane, alkylphenoxysilane, and phenylalkoxysilane. Aminoalkylalkoxysilane is preferable as the third silicone-based compound, and it is preferable to use glycidoxyalkylalkoxysilane as the fourth silicone-based compound.

The above-mentioned silicone-based resin can be obtained by applying a liquid substance of a coating layer forming material (coating liquid) to a clean gasket surface and hardening the applied liquid substance. In this case, a method of applying a liquid substance to a gasket surface can include a conventional known method such as a dipping method and a spraying method. In particular, it is preferable to spray and apply a coating liquid (splaying application) while rotating an object to be coated (specifically, for example, at 100 rpm to 600 rpm). Furthermore, the splaying application is preferably performed after a portion of the gasket to be coated is subjected to a heat treatment to reach, for example, about 60° C. to 120° C. As a result, a surface to be coated allows a coating liquid to be quickly fixed without repelling water.

The above-mentioned silicone-based resin may be made of a silicone obtained by hardening a silicone having a vinyl group and a silicone having a hydrogen group bonded with a silicon atom by means of an addition reaction using platinum as a catalyst. In accordance with an exemplary embodiment, the silicone-based resin preferably does not include solid particles. A liquid substance of a coating layer forming material (coating liquid) used for forming the coating layer is preferably an aqueous coating liquid obtained by emulsifying and dispersing a reactive silicone in water. In addition to the reactive silicone, a specific auxiliary agent for acquiring an adhesive property to a core part 2 and enhancing strength of the coating layer may be prescribed.

A coating liquid is preferably an aqueous coating liquid, and active ingredients contained in the coating liquid are roughly divided into three types. An ingredient 1 is a reactive silicone. An ingredient 2 is a reaction catalyst for the ingredient 1. An ingredient 3 is an auxiliary agent for preventing the soft coating 42 from peeling off the gasket body 41 and breaking itself. An additive agent can be further mixed as necessary. (for example, ingredient 1: reactive silicone, ingredient 2: reaction catalyst and reaction inhibitor for ingredient 1, ingredient 3: auxiliary agent).

The ingredient 1 can include an ingredient 1a and an ingredient 1b.

The ingredient 1a is an emulsion of polysiloxane containing a principal ingredient of a silicone of the soft coating 42, and the polysiloxane is polysiloxane having at least two vinyl groups in a single molecule. Examples of the polysiloxane having at least two vinyl groups in a single molecule include polydimethylsiloxane having vinyl groups at both terminals, poly(diphenylsiloxane-dimethylsiloxane) having vinyl groups at both terminals, polyphenylmethylsiloxane having vinyl groups at both terminals, poly(vinylphenylsiloxane-phenylmethylsiloxane) having vinylphenylmethyl groups at both terminals, poly(trifluoropropylmethylsiloxane-dimethylsiloxane) having vinyl groups at both terminals, poly(diethylsiloxane-dimethylsiloxane) having vinyl groups at both terminals, polyvinylmethylsiloxane, both terminals of which are trimethylsilyl groups, poly(vinylmethylsiloxane-dimethylsiloxane), both terminals of which are trimethylsilyl groups, polyvinylmethoxysiloxane, polyvinylethoxysiloxane, and poly(vinylethoxysiloxane-propylethoxysiloxane).

The ingredient 1b is an emulsion of polysiloxane containing an accessary ingredient of a silicone of the above-mentioned silicone-based resin. The ingredient 1b reacts with polysiloxane in the ingredient 1a which is the principal ingredient to function as a crosslinking agent in a silicone of the soft coating 42. The polysiloxane is polysiloxane having a hydrogen group bonded with at least two silicon atoms in a single molecule. Examples of the polysiloxane having a hydrogen group bonded with at least two silicon atoms in a single molecule include polymethylhydrosiloxane having trimethylsilyl groups at both terminals, poly(methylhydrosiloxane-dimethylsiloxane) having trimethylsilyl groups at both terminals, polyethylhydrosiloxane having trimethylsilyl groups at both terminals, poly(methylhydrosiloxane-octylmethylsiloxane) having trimethylsilyl groups at both terminals.

The ingredient 2 is, in accordance with an exemplary embodiment, a reaction catalyst for the ingredient 1a and the ingredient 1b. Specifically, the reaction catalyst is a platinum group metal-based catalyst for enhancing hydrosilylation of a vinyl group of the ingredient 1a and a hydrogen group of the ingredient 1b. Examples of the platinum group metal-based catalyst (platinum group-based catalyst) include a catalyst such as a platinum-based catalyst, a palladium-based catalyst, and a rhodium-based catalyst. Among them, a platinum-based catalyst is preferable, and specific examples of the platinum-based catalyst include a chloroplatinic acid, an alcohol-modified chloroplatinic acid, a complex of a chloroplatinic acid and ketone, a complex of platinum and an olefin, and a complex of platinum and vinylsiloxane.

The ingredient 3 is an auxiliary agent for preventing the above-mentioned silicone-based resin from peeling off the core part 2 or breaking itself, and alkylalkoxysilane, phenylalkoxysilane, alkylphenoxysilane, aminoalkylalkoxysilane, glycidoxyalkylalkoxysilane or the like is suitable.

Since the gasket 4 has the soft coating 42, the gasket 4 has a stable sliding property even in the absence of a lubricant on a sliding surface, and can maintain a sealing property in a drug housing space. Therefore, the soft coating 42 may be any substance as long as it has the above-mentioned functions.

In particular, the gasket is preferably configured such that the initial sliding resistance value is equal to or less than the maximum value of the dynamic sliding resistance value. Owing to this configuration, good initial sliding can be started, and excess initial movement does not occur.

The syringe with needle 10 has the plunger 5 attached to the gasket 4. The plunger 5 may be mounted in the gasket at the point of use.

The plunger 5 can include a body part 51, a plate part 54, a distal end part 52, and a plunger side screw part. The plate part 54 is provided at the body part 51 for pressing a rear end surface of the gasket. The distal end part 52 protrudes forward beyond the plate part 54 and can be housed in the plunger attaching part 47 of the gasket 4. The plunger side screw part is provided on an outer surface of the distal end part 52 and can be screwed with the gasket side screw part. The plunger 5 further can include a pressing part 53, a plurality of distal end part reinforcing parts 55, and a plurality of body part reinforcing parts 56. The pressing part 53 is provided at a rear end of the body part 51. The plurality of distal end part reinforcing parts 55 is provided in the vicinity of the plate part 54 and on a proximal end side. The plurality of body part reinforcing parts 56 is provided between the distal end part reinforcing parts 55 and the pressing part 53. Since the plunger 5 is provided with, at the distal end part, the plurality of reinforcing parts including the plate part, the distal end part is prevented from being deformed at the time of pressing the plunger (at the time of pressing the gasket).

Figure 2:
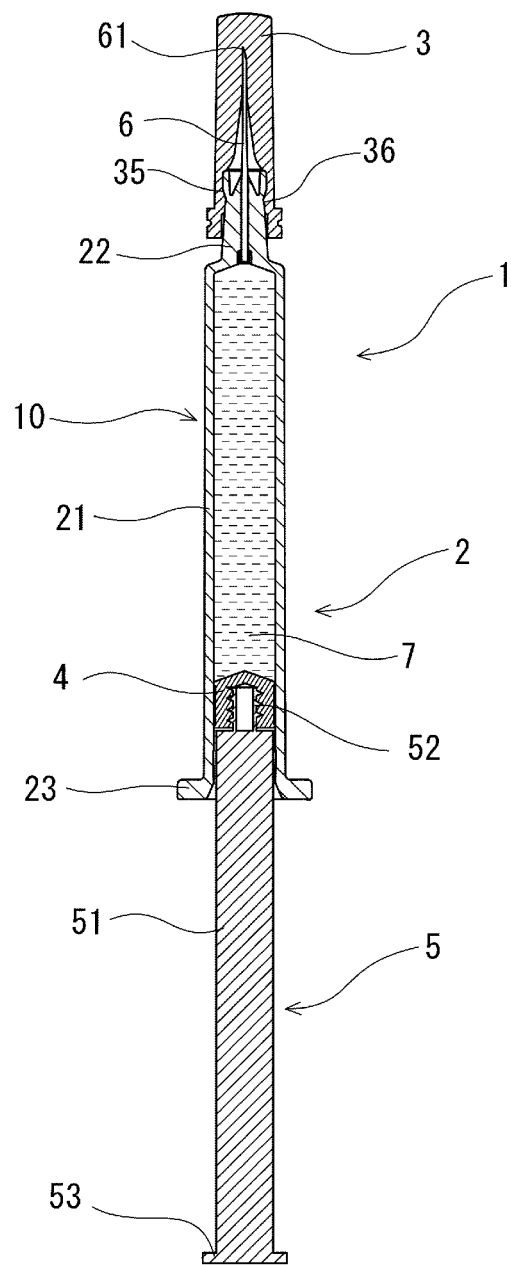
FIG. 2 is a cross-sectional view taken along line II-II of FIG. 1.
Figure 3:
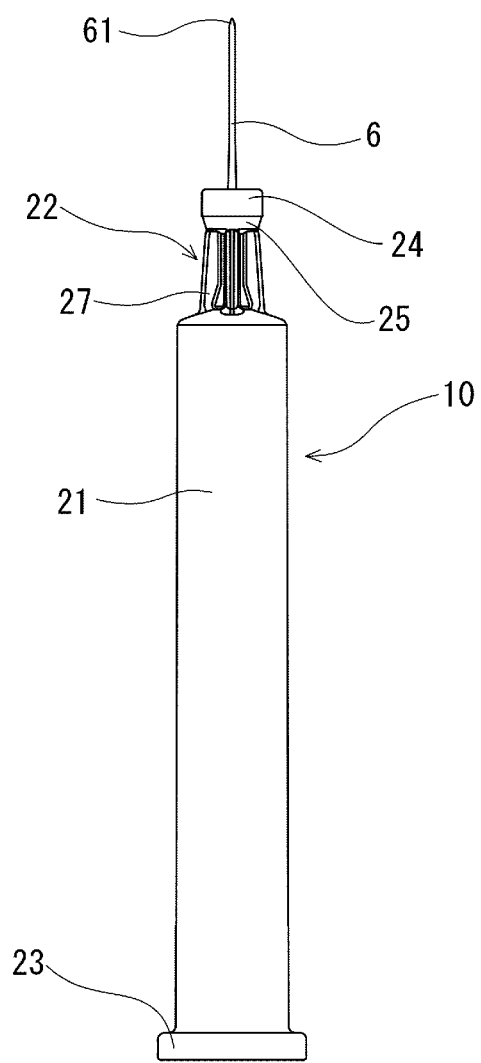
FIG. 3 is a front view of an outer cylinder used in the prefilled syringe of FIGS. 1 and 2.
Figure 4:
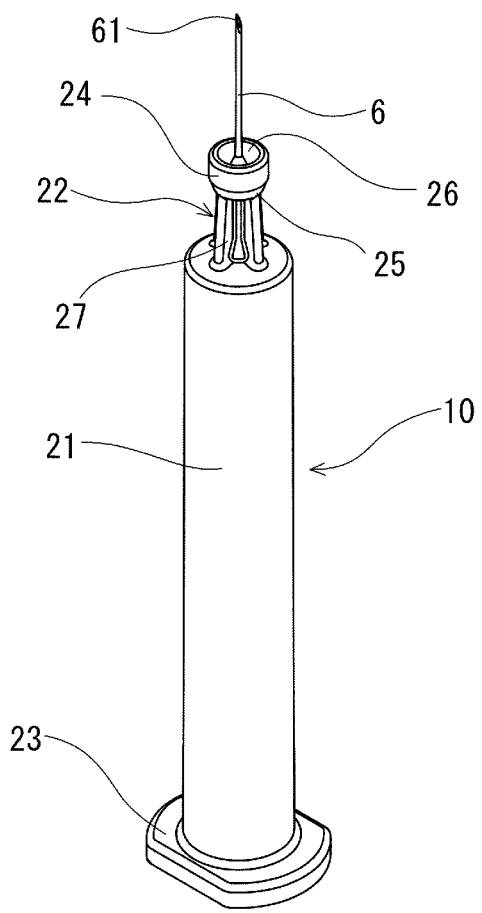
FIG. 4 is a perspective view of the outer cylinder illustrated in FIG. 3 when viewed from obliquely above.
Figure 6:
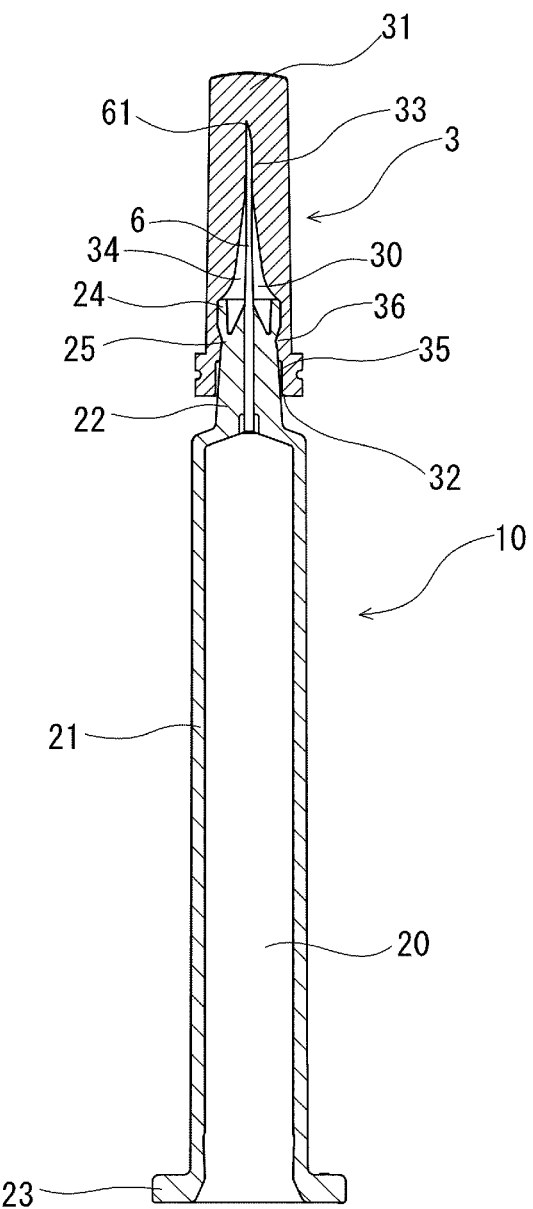
FIG. 6 is a cross-sectional view of the outer cylinder according to the present disclosure equipped with a cap.

The seal cap 3 can include, as illustrated in FIGS. 2 and 6, a closed distal end part 31, an opening proximal end part 32, a hollow part 30, a piercing enabled part 33, and a protruding part 36. The hollow part 30 can include an injection needle attaching part housing part 35 that is positioned at a distal end side beyond the opening proximal end part 32 and houses the injection needle attaching part 22, and an injection needle housing part 34 extending continuously from a distal end of the injection needle attaching part housing part 35. The piercing enabled part 33 can be pierced by the puncturing needle tip 61 of the injection needle 6 housed in the injection needle housing part 34. The protruding part 36 is formed in an inner surface of the injection needle attaching part housing part 35. When the seal cap 3 is mounted on the injection needle attaching part 22 of the outer cylinder 10, the puncturing needle tip 61 pierces the piercing enabled part 33 of the seal cap 3 to be sealed. The protruding part 36 is engaged with the annular recessed part 25 of the injection needle attaching part 22 of the outer cylinder 10, and the inner surface of the injection needle attaching part housing part 35 comes into close contact with an outer surface of the injection needle attaching part 22.

As for a forming material for the seal cap 3, at least the piercing enabled part 33 needs to be formed by an elastic material capable of being pierced by the injection needle. Preferable examples of the elastic material capable of being pierced by the injection needle include, for example, rubber such as butyl rubber, isoprene rubber, latex rubber, and silicone rubber; and elastomers such as synthetic resin elastomers (for example, styrene-based elastomers such as an SBS elastomer and an SEBS elastomer, and olefin-based elastomers such as an ethylene-α-olefin copolymer elastomer).

The seal cap 3 according to the present embodiment is configured such that at least the injection needle attaching part housing part 35 and the piercing enabled part 33 (in the present embodiment, the entire seal cap) are formed by the above-mentioned elastic material capable of being pierced by the injection needle. Therefore, when the seal cap 3 is mounted on the injection needle attaching part 22 of the outer cylinder 10, the inner surface of the injection needle attaching part housing part 35 is elastically deformed in accordance with an outer surface of the annular head part 24 of the injection needle attaching part 22. Consequently, the inner surface of the injection needle attaching part housing part 35 comes into close contact with the outer surface of the annular head part 24 of the injection needle attaching part 22, whereby unwilling detachment of the seal cap 3 from the outer cylinder 10 can be reduced.

The seal cap may be configured in any way as long as it can perform sealing and detachment without damaging the needle tip of the injection needle. A so-called rigid needle shield configured in such a manner that a cover made of rigid plastic that covers the seal cap from a distal end to a side surface is further provided at the above-mentioned injection needle attaching housing part of the seal cap 3 may be employed.

The medical liquid 7 placed in the prefilled syringe 1 is, for example, a solution, a gel, or a suspension containing a drug. A usable drug is substantially not limited as long as it is not a drug inappropriate for percutaneous administration.

Examples of the drug include, for example, a protein preparation, an antibody preparation, a hyaluronic acid, an antibacterial drug, an antiviral drug, a vaccine, an antitumor drug, an immunosuppressive drug, a steroid drug, an anti-inflammatory drug, an antirheumatic drug, an arthritis treatment drug, an antihistamine drug, an anti-allergic drug, a diabetes treatment drug, a hormone agent such as a growth hormone, a bone calcium metabolic drug, vitamins, a blood preparation, a hematinic drug, an antithrombotic drug, an anti-hyperlipidemic drug, an anti-arrhythmic drug, a vasodilating drug, prostaglandins, a calcium antagonist drug, an ACE inhibitor drug, a β blocker, an antihypertensive drug, a diuretic drug, a xanthine derivative, a β agonist, an anti-asthmatic drug, an antitussive drug, an expectorant drug, an anticholinergic drug, an anti-diarrheal drug, a stomachic digestive drug, an antiulcer drug, a purgative agent, a sleeping drug, a sedative drug, an antipyretic agent, a cold drug, an antiepileptic drug, an antipsychotic drug, an antidepressant drug, an anti-anxiety drug, a central nerve stimulant drug, a parasympathetic nerve agonist drug, a sympathetic nerve agonist drug, an antiemetic agent, a central stimulant drug, an anti-parkinson drug, a muscle relaxant drug, an antispasmodic drug, an anesthetic drug, an antipruritic drug, an anti-migraine drug, oligonucleotides, and a gene drug. In particular, the syringe with needle according to the present disclosure is particularly effective when it is used for a drug having a viscosity of, for example, 10 mPa·s or more.

Next, a medical liquid administration tool 100 according to the present disclosure will be described using an example illustrated in FIGS. 10 to 15.

The medical liquid administration tool 100 according to the present example can include an autoinjector and the above-mentioned prefilled syringe mounted in the autoinjector.

The autoinjector of the medical liquid administration tool 100 can include a cylindrical sheath 106, a gasket pressing means 102, a protector 103, and a regulating means 107. The gasket pressing means 102 is housed in the cylindrical sheath 106. The protector 103 houses the prefilled syringe 1. The regulating means 107 regulates movement of the gasket pressing means 102. Furthermore, the medical liquid administration tool 100 can be set to an injection needle housing state, an administration enabled state, an administration state, and an injection needle rehousing state. In the injection needle housing state (first state), the protector 103 houses the needle tip 61 of the injection needle 6. In the administration enabled state (for example, liquid discharging preparation completion state or second state), the cylindrical sheath 106 moves to a distal end side, whereby the needle tip 61 protrudes beyond the protector 103, and the gasket 4 is enabled to move in a distal end direction by means of the gasket pressing means 102. In the administration state (for example, liquid discharging state or third state), the gasket 4 is pressed by the gasket pressing means 102 and moved in the distal end direction, whereby the medical liquid 7 is discharged from the injection needle 6. In the injection needle rehousing state (fourth state), the cylindrical sheath 106 moves to a proximal end side, whereby the needle tip 61 of the injection needle 6 is housed in the protector 103.

The protector 103 has an external engaging piece 133 that is provided on a side wall of the protector 103 and elastically deformed. An engaging cylindrical member 125 has an internal engaging piece 252 that is provided on a proximal end part of the engaging cylindrical member 125, engaged with the external engaging piece in the injection needle rehousing state, and elastically deformed. The gasket pressing means 102 has the engaging cylindrical member 125 that presses and deforms the internal engaging piece 252 toward the outside in the injection needle rehousing state. In the injection needle rehousing state, the internal engaging piece is pressed toward the outside by the engaging cylindrical member 125 and engaged with the external engaging piece, thereby preventing the protector from moving in a proximal end direction.

In the medical liquid administration tool 100, installation of a button or the like for a puncture operation can be omitted, resulting in a simple structure. Furthermore, after the puncture, the engaging cylindrical member 125 can be prevented from moving again in the distal end direction, thereby preventing the needle tip of the injection needle from protruding again from a distal end opening of the protector.

The gasket pressing means 102 can include a gasket pressing member 124 and the engaging cylindrical member 125. A distal end part of the gasket pressing member 124 is connected to a rear end part of the gasket 4 of the prefilled syringe 1. The engaging cylindrical member 125 is mounted on a proximal end side portion of the outer cylinder 10 of the prefilled syringe 1. A cylindrical distal end part 136 of the protector 103 protrudes beyond the cylindrical sheath 106.

Figure 10:
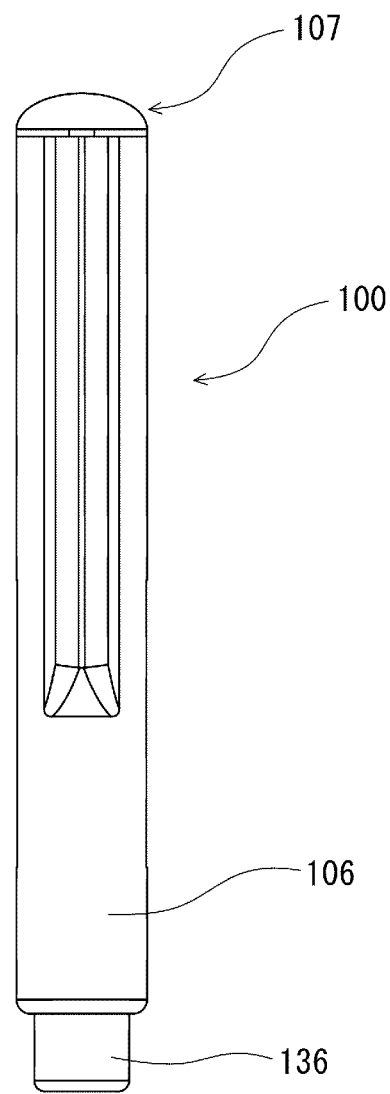
FIG. 10 is a front view of a medical liquid administration tool in which the prefilled syringe according to the present disclosure is used.
Figure 12:
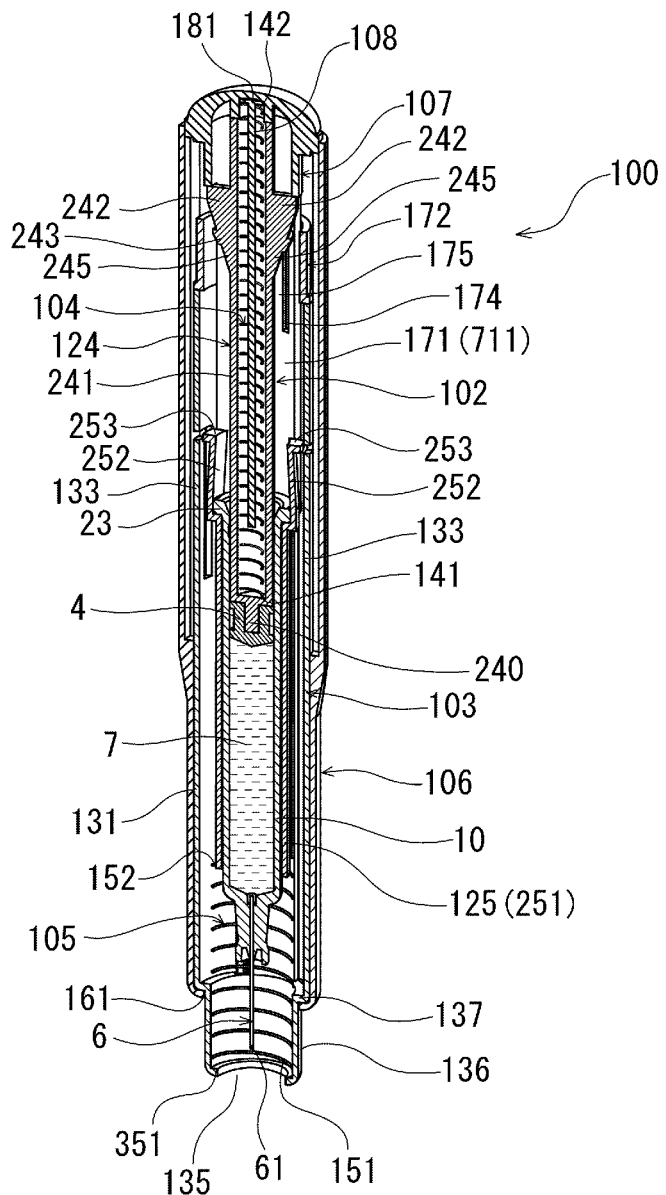
FIG. 12 is an explanatory view for explaining the internal structure and operation of the medical liquid administration tool illustrated in FIG. 10.

In the medical liquid administration tool 100 according to the present example, the entire injection needle 6 including the needle tip 61 is housed in the protector 103 constituting a distal end part of the medical liquid administration tool 100 in a state (seal cap detachment state) illustrated in FIGS. 10 and 12. The needle tip 61 is positioned within the cylindrical distal end part 136 of the protector 103.

Figure 13:
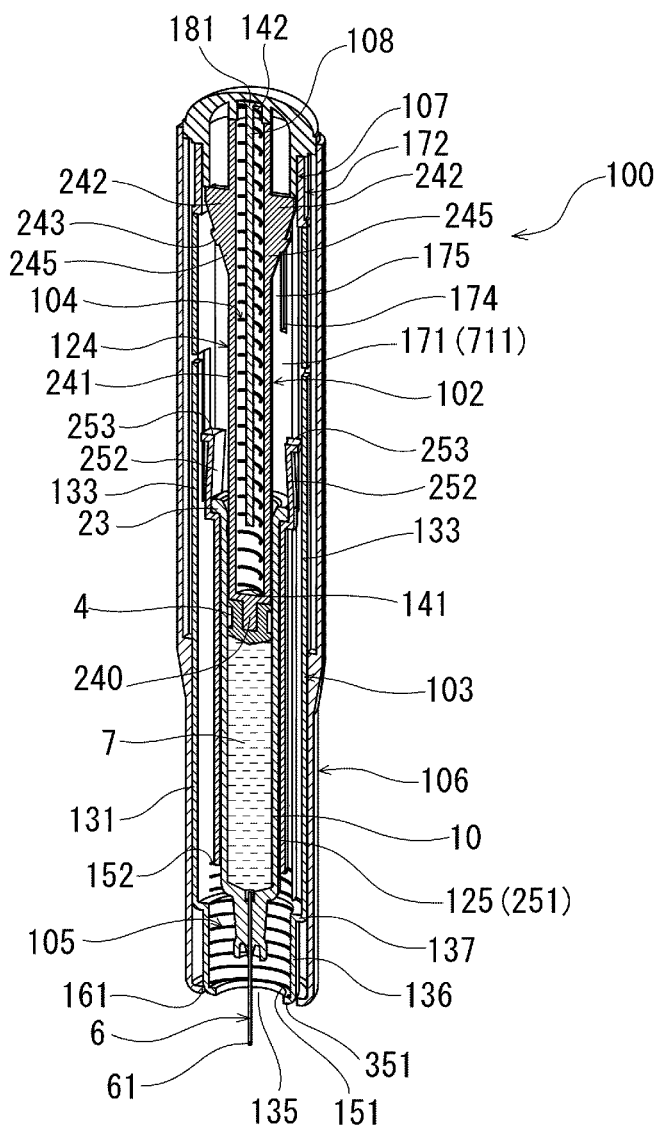
FIG. 13 is an explanatory view for explaining the internal structure and the operation of the medical liquid administration tool illustrated in FIG. 10.
Figure 14:
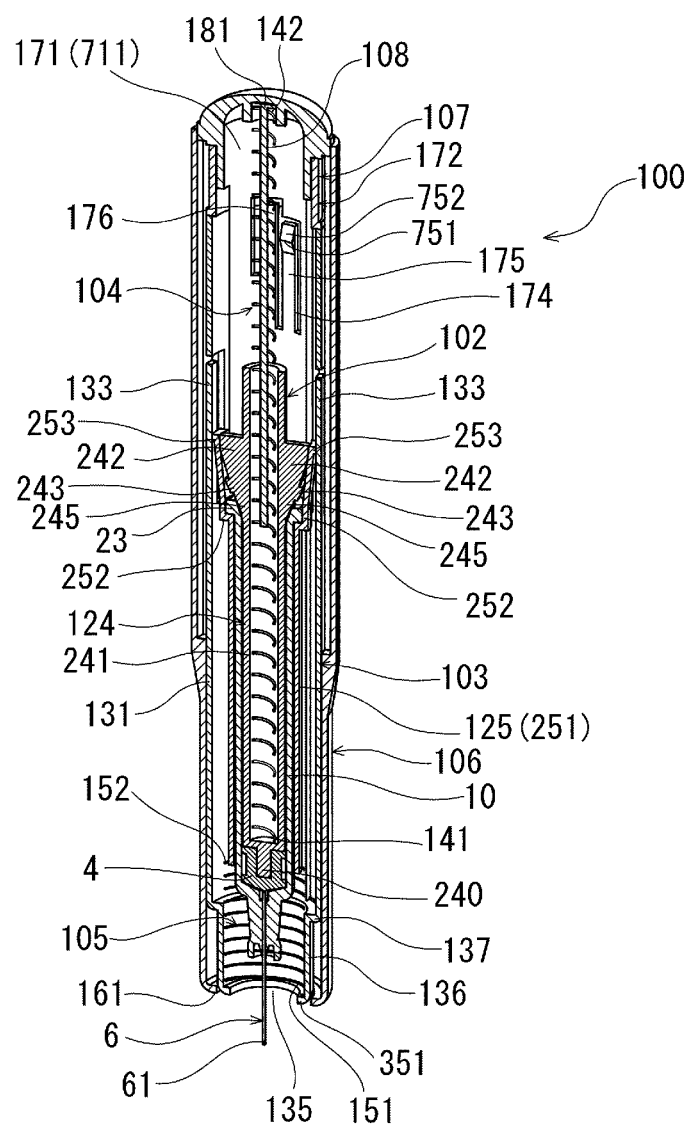
FIG. 14 is an explanatory view for explaining the internal structure and the operation of the medical liquid administration tool illustrated in FIG. 10.
Figure 15:
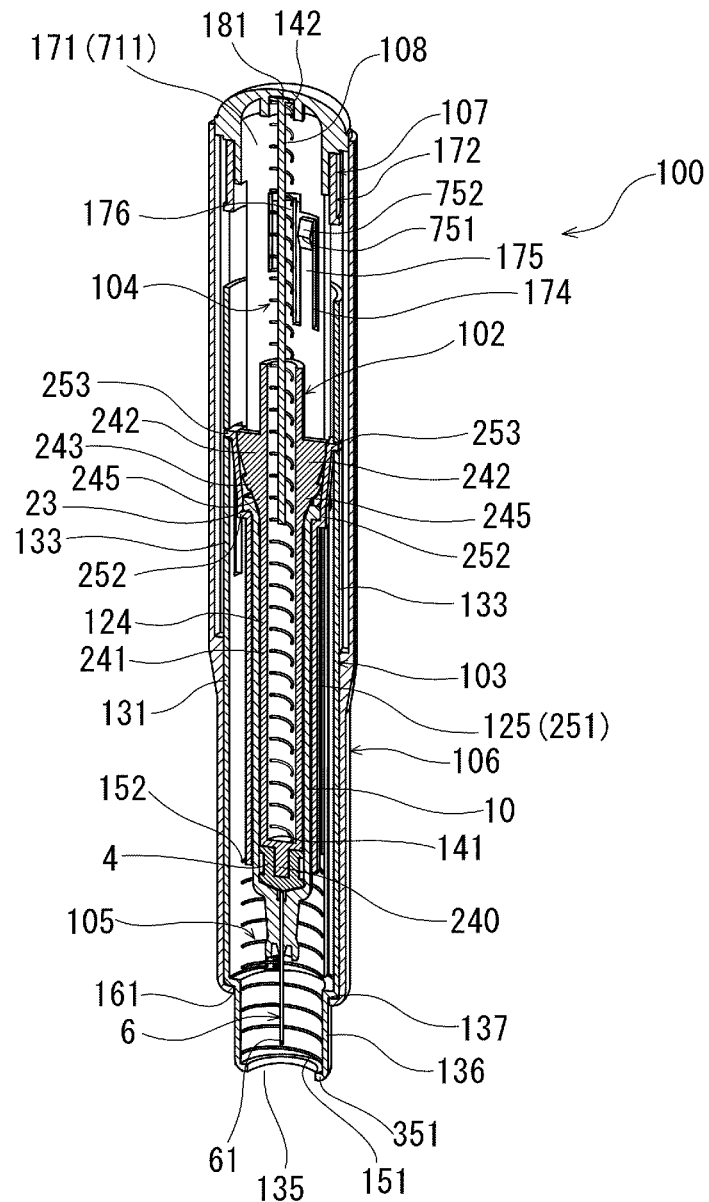
FIG. 15 is an explanatory view for explaining the internal structure and the operation of the medical liquid administration tool illustrated in FIG. 10.

The cylindrical sheath 106 moves to the distal end side when the cylindrical distal end part 136 of the medical liquid administration tool 100 is pressed against a site for administration, and the cylindrical sheath 106 is pushed in a direction toward the site for administration with force exceeding energizing force of a second energizing member 105. In other words, when viewed from the entire medical liquid administration tool, the protector 103 relatively moves back in the proximal end direction. Consequently, the cylindrical sheath 106 and a first regulating member 171, the gasket pressing means 102, and the prefilled syringe 1 fixed to the cylindrical sheath 106 move forward, whereby the injection needle 6 protrudes as illustrated in FIG. 13 to puncture the site for administration. At the same time, movement regulation for the gasket pressing member 124 by a second regulating member 172 is released, whereby the gasket pressing member 124 is pressed by a first energizing member 104 to move forward and press the gasket 4 as illustrated in FIG. 14. The medical liquid 7 within the prefilled syringe 1 then passes through the injection needle 6 to be injected into a living body. After the administration is completed, the press of the cylindrical sheath 106 to the site for puncture is released as illustrated in FIG. 15, whereby the syringe 1 is pushed back by the second energizing member 105 to move to the proximal end side. As a result, the injection needle 6 is housed again in the protector 103.

Figure 11:
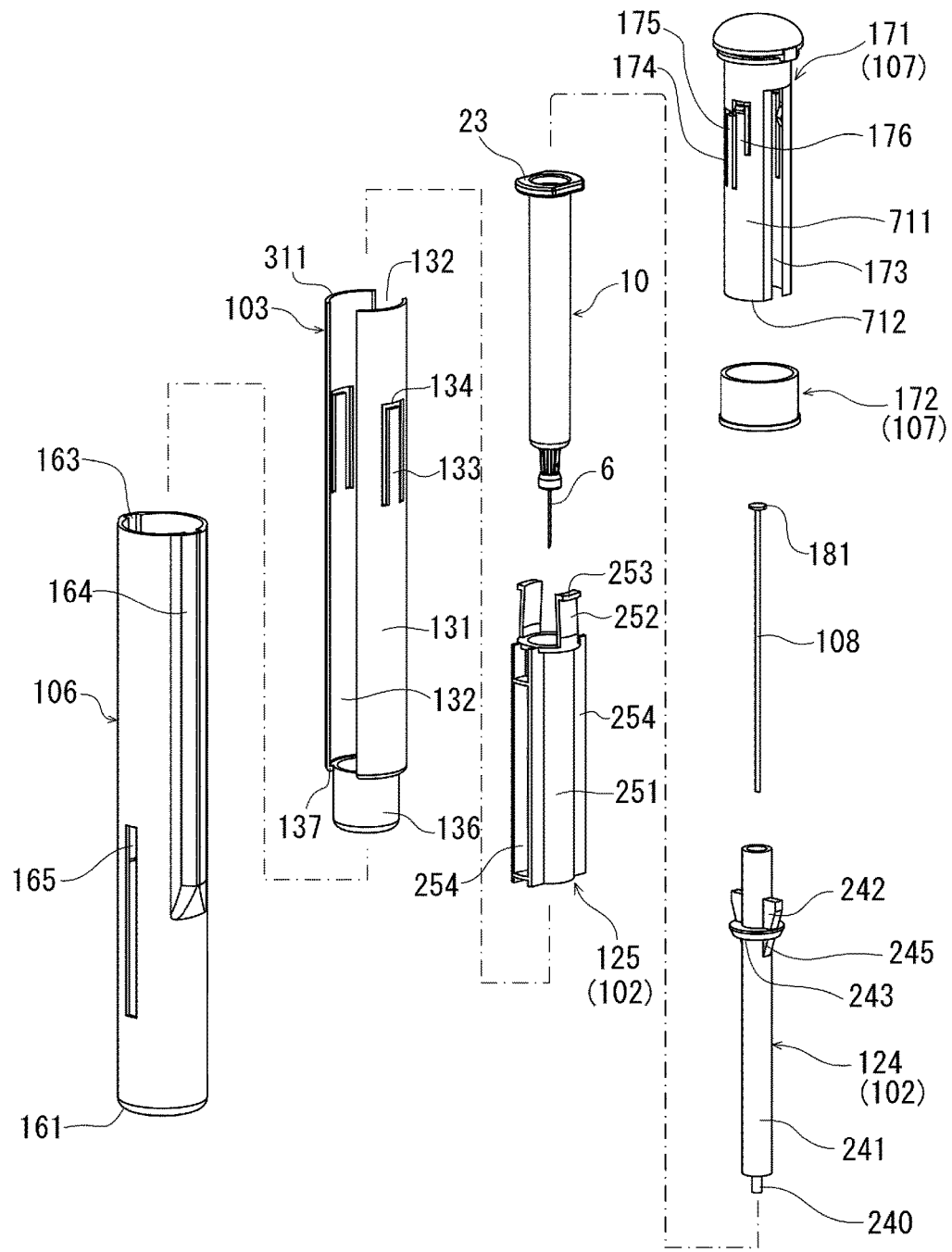
FIG. 11 is an explanatory view for explaining an internal structure of the medical liquid administration tool illustrated in FIG. 10.

In the medical liquid administration tool 100 according to the present example, the engaging cylindrical member 125 has, as illustrated in FIG. 11, a cylindrical part 251 that covers an outer peripheral part of the proximal end part of the outer cylinder 10 of the syringe 1. A proximal end surface of the cylindrical part 251 allows the flange 23 of the outer cylinder 10 to be locked, thereby regulating movement of the outer cylinder 10 in the distal end direction with respect to the engaging cylindrical member 125. At an edge part of a proximal end opening part of the cylindrical part 251, two internal engaging pieces 252 protruding toward the proximal end direction are formed. The internal engaging pieces 252 are formed to face each other with respect to a central axis of the cylindrical part 251.

Each of the internal engaging pieces 252 can be elastically deformed, and can be brought closer to and separated from the other internal engaging piece 252. Each of the internal engaging pieces 252 has, at an outer surface of a proximal end, a claw 253 protruding toward the outside. The claw 253 is positioned at a proximal end side of the flange 23 of the outer cylinder 10 of the mounted syringe 1. As illustrated in FIG. 11, the claw 253 can be engaged with the external engaging piece 133 of the protector 103, which will be described later. The engaging cylindrical member 125 can include, at an outer peripheral part of the cylindrical part 251, two guide parts 254 extending and protruding in the axial direction. The two guide parts 254 are formed to face each other with respect to the central axis of the cylindrical part 251. The two guide parts 254 and the two internal engaging pieces 252 are arranged so as not to overlap one another in the axial direction. Specifically, a virtual line connecting centers of the two guide parts 254 and a virtual line connecting centers of the two internal engaging pieces 252 are substantially orthogonal to each other.

In the medical liquid administration tool 100 according to the present example, as illustrated in FIG. 11, the gasket pressing member 124 has an elongated and hollow body part 241, two pressing protruding parts 242, and an annular engaging part 243. The body part 241 has a gasket connecting part 240 at a distal end, and a distal end side part can enter the outer cylinder 10. The two pressing protruding parts 242 are formed on a side surface of a proximal end part of the body part 241 so as to face each other. The engaging part 243 is provided in the vicinity of distal ends of the pressing protruding parts 242. Each of the pressing protruding parts 242 is provided for pressing and deforming the above-mentioned internal engaging piece 252 of the engaging cylindrical member 125 to the outside.

As illustrated in FIG. 11, each of the pressing protruding parts 242 extends in the axial direction of the body part 241 with a predetermined width by a predetermined length, and can include, at a portion at the distal end side, such an inclining surface 245 that a protruding height is reduced toward the distal end direction. Therefore, when the gasket pressing member 124 moves toward the distal end direction, the two pressing protruding parts 242 facilitate the entrance of the engaging cylindrical member 125 between the two internal engaging pieces 252. A maximum distance between the two pressing protruding parts 242 is larger than a minimum distance between the two internal engaging pieces 252 in a natural state where no external force is applied. The annular engaging part 243 constitutes a part of the regulating means 107, which will be described later. In the same way as the inclining surface 245 of the pressing protruding part 242, the engaging part 243 can include an annular inclining surface that is reduced in diameter toward a distal end side.

The medical liquid administration tool 100 can include the protector 103 extending in the axial direction. The protector 103 partially covers the gasket pressing means 102 in which the prefilled syringe 1 has been mounted. As illustrated in FIG. 11, the protector 103 can include two gutter-shaped side wall parts 131 each having an arc-shaped cross section and extending by a predetermined length so that the two gutter-shaped side wall parts 131 face each other. A pair of side part opening parts 132 having a predetermined width and extending by a predetermined length is formed between the two gutter-shaped side wall parts 131. The protector 103 can include the cylindrical distal end part 136 and a step part 137. The cylindrical distal end part 136 is connected to distal ends of the two gutter-shaped side wall parts 131. The step part 137 is formed between an outer surface of the cylindrical distal end part 136 and the distal ends of the gutter-shaped side wall parts 131.

The gutter-shaped side wall parts 131 of the protector 103 can include two slits 134 each extending from a central part to a proximal end side and formed in an inverted U shape (in other words, such a substantially U shape that an opening part faces downward). The two slits 134 are formed to face each other with respect to a central axis of the protector 103. A portion surrounded by each of the slits 134 forms the external engaging piece 133 that can be elastically deformed. The external engaging piece 133 can be engaged with the internal engaging piece 252 of the gasket pressing means 102.

An opening end 351 of the cylindrical distal end part 136 of the protector 103 serves as a part that abuts on a surface of a living body when the medical liquid is administered to the living body using the medical liquid administration tool 100.

In accordance with an exemplary embodiment, the protector 103 can be set to the four states illustrated in FIGS. 12 to 15.

In the injection needle housing state, as illustrated in FIGS. 10 and 12, the prefilled syringe 1 houses the medical liquid, and the distal end opening 135 of the protector 103 is positioned at a distal end side beyond the needle tip 61 of the injection needle 6, whereby the injection needle 6 is not exposed. In the administration enabled state, as illustrated in FIG. 13, the protector 103 moves to the proximal end side, and the needle tip 61 of the injection needle 6 protrudes from the distal end opening 135 of the protector 103, whereby the gasket 4 is enabled to move toward the distal end direction.

In the administration state, as illustrated in FIG. 14, the gasket 4 moves in the distal end direction, whereby the medical liquid is ejected through the injection needle 6. In the injection needle rehousing state, as illustrated in FIG. 15, the distal end opening 135 of the protector 103 is positioned again at the distal end side beyond the needle tip 61 of the injection needle 6, whereby the injection needle 6 is rehoused. In this injection needle rehousing state, the internal engaging piece 252 of the engaging cylindrical member 125 is pushed by each of the pressing protruding parts 242 of the gasket pressing member 124 toward the outside to be engaged with the external engaging piece 133 of the protector 103, thereby regulating movement of the protector 103 in the proximal end direction.

The medical liquid administration tool 100 according to the present example can include the first energizing member 104 and the second energizing member 105. The first energizing member 104 is housed in the gasket pressing member 124. A coil spring extending in an axial direction of the gasket pressing member 124 is used as the first energizing member 104. The second energizing member 105 is housed in a distal end part of the protector 103. A coil spring extending in an axial direction of the protector 103 is used as the second energizing member 105. A distal end of the coil spring 105 abuts on an internal annular rib provided on an inner surface of the distal end of the protector 103. A proximal end of the coil spring 105 abuts on a distal end of the engaging cylindrical member 125.

In the administration state illustrated in FIG. 14, the coil spring 104 energizes, through the gasket pressing member 124, the gasket 4 toward the distal end direction. In the injection needle housing state illustrated in FIG. 12, the coil spring 105 energizes the protector 103 toward the distal end direction such that the distal end opening 135 of the protector 103 is positioned at the distal end side beyond the needle tip 61. When shifting to the injection needle rehousing state illustrated in FIG. 15, the coil spring 105 energizes the protector 103 in the distal end direction.

The coil spring 104 is arranged within the gasket pressing member 124 of the gasket pressing means 102 in a compressed state. A distal end 141 of the coil spring 104 abuts on a closed distal end part of an inner cavity of the body part 241 of the gasket pressing member 124. A proximal end 142 of the coil spring 104 abuts on a flange 181 formed at a proximal end part of a buckling preventing member 108 inserted into the coil spring 104. Consequently, the gasket 4 is securely energized toward the distal end direction. The buckling preventing member 108 prevents the coil spring 104 from buckling, i.e. bending, when the coil spring 104 is contracted. The buckling preventing member 108 is a rod-shaped member capable of being inserted into the coil spring 104.

The coil spring 105 is housed in the distal end part of the protector 103 in a compressed state. A distal end part of the syringe 1 enters a proximal end part of the coil spring 105. A distal end 151 of the coil spring 105 abuts on a proximal end side of an edge part of the distal end opening 135 of the protector 103. A proximal end 152 of the coil spring 105 abuts on the engaging cylindrical member 125. Consequently, the coil spring 105 securely energizes the protector 103 in a rear end direction.

In the injection needle housing state illustrated in FIG. 12, the regulating means 107 regulates movement of the gasket pressing member 124 of the gasket pressing means 102 in the distal end direction. In the administration enabled state illustrated in FIG. 13, the regulating means 107 releases the regulation for the gasket pressing member 124. In the present example, the regulating means 107 can include the tubular first regulating member 171 and the ring-shaped second regulating member 172 such that a distal end surface of the regulating means 107 abuts on a proximal end surface of the outer cylinder 10. The first regulating member 171 is provided in a fixed manner with respect to the outer cylinder 10. The second regulating member 172 is movably arranged on an outer peripheral side of the first regulating member 171.

As illustrated in FIG. 11, the first regulating member 171 can include two gutter-shaped side wall parts 711 each having an arc-shaped cross section and extending by a predetermined length so that the two gutter-shaped side wall parts 711 face each other. The first regulating member 171 is formed between the two gutter-shaped side wall parts 711 and can include a pair of side part opening parts 173 extending from a distal end surface 712 by a predetermined length in a longitudinal direction. The pressing protruding part 242 of the gasket pressing member 124 enters each of the side part opening parts 173. The engaging part 243 of the gasket pressing member 124 and an elastic piece 175 provided at the gutter-shaped side wall part 711 which will be described later are positioned at the same circumferential direction portion of the gasket pressing member 124. When the gasket pressing member 124 is moved, the moving gasket pressing member 124 is guided by the pressing protruding part 242 and the side part opening part 173.

A slit 174 is formed in each of the gutter-shaped side wall parts 711 of the first regulating member 171. The slit 174 can include three axial direction slits arranged in parallel to one another and two circumferential direction slits coupling the adjacent axial direction slits. A portion surrounded by the slits 174 constitutes the elastic piece 175 and an elastic piece 176 that can be elastically deformed.

The elastic piece 175 can be elastically deformed, and can be brought closer to and separated from the engaging part 243 of the gasket pressing member 124. A projecting part 751 is formed on an inner surface of the elastic piece 175. At a proximal end part of the projecting part, such an inclining surface 752 that a protruding height is reduced toward a proximal end is formed. This inclining surface abuts on the above-mentioned inclining surface 245 of the engaging part 243 of the gasket pressing member 124. Consequently, force to the outside is applied to the inclining surface of the elastic piece 175 as the gasket pressing member 124 moves in the distal end direction, whereby the elastic piece 175 is easily deformed toward the outside and separated from the engaging part 243. Each of the gutter-shaped side wall parts 711 of the first regulating member 171 is housed in a rear end part of the cylindrical sheath 106, and the first regulating member 171 is fixed to the cylindrical sheath 106 at the rear end part.

The second regulating member 172 can move from a regulating position where an inner peripheral surface of the second regulating member 172 is in contact with an outer surface of the elastic piece 175 to a releasing position where the inner peripheral surface is positioned at a proximal end side beyond the elastic piece 175. Furthermore, a distal end surface of the second regulating member 172 is in contact with a proximal end surface of the protector 103. Consequently, the second regulating member 172 moves in the proximal end direction as the protector 103 moves in the proximal end direction.

The elastic piece 176 of the first regulating member 171 can be elastically deformed, and can be brought closer to and separated from a proximal end surface of the second regulating member 172. The elastic piece 176 can include, at a proximal end part thereof, a projecting part provided on an outer surface. Furthermore, a distal end part of the projecting part can include such an inclining surface that a protruding height is reduced toward a distal end direction. Consequently, force to the inside is applied to the inclining surface as the second regulating member 172 moves in the proximal end direction, whereby the elastic piece 176 is easily deformed toward the inside and separated from the second regulating member 172.

In the injection needle housing state illustrated in FIG. 12, the elastic piece 175 of the first regulating member 171 is engaged with the annular engaging part 243 of the gasket pressing member 124. The second regulating member 172 is located at the regulating position to regulate the deformation of the elastic piece 175 to the outside. Furthermore, the projecting part (not illustrated) of the elastic piece 176 is engaged with the proximal end surface of the second regulating member 172 to prevent the second regulating member 172 from unintentionally moving in the proximal end direction. Consequently, the engaged state of the elastic piece 175 and the engaging part 243 is maintained, whereby the gasket pressing member 124 does not move in the distal end direction.

In order to shift to the administration enabled state illustrated in FIG. 13, the protector 103 moves in the proximal end direction, and the elastic piece 176 is deformed toward the inside, whereby the engagement with the proximal end surface of the second regulating member 172 is released. The second regulating member 172 moves in the proximal end direction to the releasing position. The elastic piece 175 is deformed toward the outside, whereby the engagement of the elastic piece 175 and the engaging part 243 is released, and the gasket pressing member 124 is enabled to move in the distal end direction.

When the second regulating member 172 is located at the releasing position, energizing force of the coil spring 104 is set to such a sufficient level as to deform, through the engaging part 243, the elastic piece 175 toward the outside and release the engagement of the elastic piece 175 and the engaging part 243. Consequently, the gasket pressing member 124 can be securely pushed and moved forward in the distal end direction by the coil spring 104.

The cylindrical sheath 106 houses the protector 103 such that the protector 103 is slidable in the axial direction. The rear end part of the cylindrical sheath 106 is fixed to the first regulating member 171. The cylindrical sheath 106 is provided with two bulge parts 164 extending in the axial direction such that the two bulge parts 164 face each other. The sheath 106 can include a window part 165. The cylindrical sheath 106 can include, as illustrated in FIG. 11, two grooves 163 extending in the axial direction in an inner surface.

In the present example, the grooves 163 are formed inside the bulge parts 164. The grooves 163 are formed to face each other with respect to a central axis of the cylindrical sheath 106. When the external engaging piece 133 of the protector 103 is pushed and widened toward the outside by the pressing protruding part 242 of the gasket pressing member 124, the external engaging piece 133 enters the groove 163, whereby the gasket pressing member 124 can move smoothly.

An inner diameter of a distal end opening of the cylindrical sheath 106 is reduced. The step part 137 of the protector 103 abuts on the inside of the reduced diameter distal end opening 161. Consequently, the protector 103 is prevented from being detached from the distal end of the cylindrical sheath 106.

EXAMPLE 1

As a forming material for a syringe outer cylinder, a cyclic olefin resin (trade name: ZEONEX (registered trademark), manufactured by Zeon Corporation) was used, and a syringe outer cylinder formed in the shape illustrated in FIG. 6 was produced by mean of insert molding using an injection needle which will be described later. A columnar portion of the syringe outer cylinder had an inner diameter of 6.3 mm and a length of 64 mm. As a forming material for a plunger, polypropylene was used, and a plunger formed in the shape illustrated in FIGS. 1 and 2 was produced by means of injection molding.

As an injection needle, a tapered needle made of stainless steel and having a distal end outer diameter of 0.34 mm, a distal end inner diameter of 0.24 mm, a proximal end outer diameter of 0.41 mm, a proximal end inner diameter of 0.31 mm, and a total length of 14 mm was produced. This tapered needle had a distal end part extending by about 6.5 mm with substantially the same outer diameter, a proximal end part extending by about 4.5 mm with substantially the same outer diameter, and about 3 mm of a tapered part provided between the distal end part and the proximal end part. An inner surface of this tapered needle had an average roughness (Ra) of less than 0.3 μm.

Using this injection needle, an outer cylinder with a needle having the formation illustrated in FIGS. 2 to 5 was produced by means of insert molding.

A gasket body of a syringe gasket formed in the shape illustrated in FIGS. 8 and 9 can be produced using butyl rubber. The gasket body was produced by subjecting, to press molding, a vulcanizable rubber composition obtained by mixing an additive agent in the butyl rubber. The obtained gasket body was formed in such a shape that a length was 7.5 mm, outer diameters at a distal end side annular rib portion and a rear end side annular rib portion were 6.8 mm, and a plunger attaching recessed part having a female screw part on the inside was included.

Next, 29 pts.wt. (parts by weight) of a silicone-based resin and 1 pts.wt. of a dioctyltin dilaurate are added to 66 pts.wt. of purified water to prepare a gasket coating liquid. The silicone-based resin is obtained by mixing the following substances using a linear chain alkylbenzene sodium sulfonate.

1) 25 pts.wt. of a trade name 1501 Fluid (manufactured by Dow Corning Toray Co., Ltd.), a principal ingredient of which is both-terminal silanol polydimethylsiloxane;

2) 0.1 pts.wt. of a trade name Z-6366 (manufactured by Dow Corning Toray Co., Ltd.), a principal ingredient of which is methyltrimethoxysilane;

3) 1 pts.wt. of a mixture of a trade name Z-6011 (manufactured by Dow Corning Toray Co., Ltd.), a principal ingredient of which is 3-aminopropyltriethoxysilane and an ethanol solution of maleic anhydride (resin ratio is 50%); and 4) 0.5 pts.wt. of a trade name Z-6040 (manufactured by Dow Corning Toray Co., Ltd.), a principal ingredient of which is 3-glycidoxypropyltrimethoxysilane.

The gasket body manufactured in the above-mentioned way in an environment of room temperature and normal pressure was subjected to a heat treatment at 90° C. for 30 minutes. After that, the gasket body was rotated (300 rpm) around its central axis, and the coating liquid with the above-mentioned composition was sprayed and applied from a rotating side surface side of the gasket. After that, the gasket body was dried at 150° C. for 30 minutes, whereby the gasket according to the present disclosure was produced. After that, the produced gasket was washed with purified water of 80° C. or more to wash off the excess coating liquid on the gasket. A coating layer formed on a surface of the gasket body had an average thickness of about 8 μm.

A syringe with needle (Example 1) according to the present disclosure was produced using the above-mentioned outer cylinder with the needle, gasket, and plunger.

COMPARATIVE EXAMPLE 1

A syringe with needle (Comparative Example 1) was produced in the same way as Example 1 except that a thin straight needle made of stainless steel and having an outer diameter of 0.34 mm, an inner diameter of 0.24 mm, and a thickness of 0.05 mm was used as an injection needle.

COMPARATIVE EXAMPLE 2

A syringe with needle (Comparative Example 2) was produced in the same way as Example 1 except that the gasket body (without a coating layer) of Example 1 to which silicone oil (manufactured by Dow Corning Toray Co., Ltd.) was applied was used as a gasket.

COMPARATIVE EXAMPLE 3

A syringe with needle (Comparative Example 3) was produced in the same way as Example 1 except that a thin straight needle made of stainless steel and having an outer diameter of 0.34 mm, an inner diameter of 0.24 mm, and a thickness of 0.05 mm was used as an injection needle, and the gasket body (without a coating layer) of Example 1 to which silicone oil (manufactured by Dow Corning Toray Co., Ltd.) was applied was used as a gasket.

EXPERIMENT 1

In 30 mL of water, 6.45 g of polyethylene glycol (trade name: polyethylene glycol 20,000, manufactured by Wako Pure Chemical Industries, Ltd.) having a molecular weight of 20,000 was dissolved to produce a viscosity adjusted solution having a viscosity of 47.5 mPa·s. The viscosity was measured using a vibration type viscometer (model name: VISCOMATE VM-100A, manufactured by SEKONIC CORPORATION and CBC Co., Ltd.).

Then, Example 1, Comparative Examples 1 to 3 were each prepared by being filled with 1.2 ml of the above-mentioned viscosity adjusted solution and stored at 40° C. for 2 days. A sliding resistance value of each syringe was measured by a universal testing machine (model name: EZ-Test, company name: Shimadzu Corporation). Specifically, a distal end of the syringe and a rear end of the plunger were fixed to a measurement object fixing part of the Autograph, and an initial sliding resistance value and a maximum sliding resistance value (N) obtained when the plunger was lowered (load cell: 500 N) by 30 mm at a speed of 200 mm/min were measured. The results are shown in Table 1.

TABLE 1

|  | Initial sliding value | Maximum sliding resistance value |
|---|---|---|
| Example 1 | 2.1N | 19.9N |
| Comparative Example 1 | 1.8N | 31.2N |
| Comparative Example 2 | 5.8N | 24.0N |
| Comparative Example 3 | 5.8N | 32.5N |

As the result of this experiment, it was found that the syringe of Example 1 had a sufficiently low initial sliding value and had a lower dynamic sliding resistance value than the syringes of all Comparative Examples, whereby an administering operation can be easily performed.

EXAMPLE 2

As an injection needle, a tapered needle made of stainless steel and having a distal end outer diameter of 0.33 mm, a distal end inner diameter of 0.23 mm, a proximal end outer diameter of 0.56 mm, a proximal end inner diameter of 0.46 mm, and a total length of 22.1 mm was produced. This tapered needle had a distal end part extending by 8.7 mm with substantially the same outer diameter, a proximal end part extending by 7.9 mm with substantially the same outer diameter, and 5.5 mm of a tapered part provided between the distal end part and the proximal end part. An inner surface had an average roughness (Ra) of less than 0.3 µm.

A syringe with needle (Example 2) was produced in the same way as Example 1 except that the above-mentioned tapered needle was used as an injection needle.

COMPARATIVE EXAMPLE 4

A syringe with needle (Comparative Example 4) was produced in the same way as Example 1 except that a thin straight needle made of stainless steel and having an outer diameter of 0.33 mm, an inner diameter of 0.23 mm, and a thickness of 0.05 mm was used as an injection needle.

EXPERIMENT 2

[Preparation of Test Solution]
Production of Test Solution A

In 27.5 mL of water, 22.5 g of glycerin (manufactured by Kanto Chemical Co., Inc.) was dissolved to produce a test solution A (viscosity: 3.987 mPa·s). Production of Test Solution B;

In 15 mL of water, 35 g of the same glycerin used for producing the test solution A was dissolved to produce a test solution B (viscosity: 17.55 mPa·s).
Production of Test Solution C In 7.5 mL of water, 42.5 g of the same glycerin used for producing the test solution A was dissolved to produce a test solution C (viscosity: 74.01 mPa·s).
Production of Test Solution D Xolair for s.c. injection 150 mg (manufactured by Novartis Pharma K.K.) which is a therapeutic agent for bronchial asthma [humanized anti-human IgE monoclonal antibody (omalizumab) preparation] and contained in a vial bottle was prepared. To the above-mentioned drug, 2.5 ml of distilled water for injection was added to produce a test solution D (viscosity: 9.456 mPa·s).

Production of Test Solution E

To the same drug used for producing the test solution D, 2.0 ml of distilled water for injection was added to produce a test solution E (viscosity: 18.37 mPa·s).
Production of Test Solution F To the same drug used for producing the test solution D, 1.4 ml of distilled water for injection was added to produce a test solution F (viscosity: 72.30 mPa·s).
Production of Test Solution G To the same drug used for producing the test solution D, 1.0 ml of distilled water for injection was added to produce a test solution G (viscosity: 269.6 mPa·s).

The viscosity was measured using a vibration type viscometer (model name: VISCOMATE VM-100A, manufactured by SEKONIC CORPORATION and CBC Co., Ltd.).

Then, Example 2 and Comparative Example 4 were filled with 1.2 ml of each of the above-mentioned test solutions such that three syringes were prepared for each solution. A sliding resistance value of each syringe was measured by a universal testing machine (model name: EZ-Test, company name: Shimadzu Corporation). Specifically, a distal end of the syringe and a rear end of the plunger were fixed to a measurement object fixing part of the universal testing machine, and a maximum sliding resistance value (N) obtained upon extrusion at an extrusion speed of 6 ml/min was measured. The results are shown in Table 2.

TABLE 2

|  | Viscosity (mPa · s) | Example 2 | Comparative Example 4 |
|---|---|---|---|
| Test Solution A | 3.987 | 4.54 ± 0.34N | 6.69 ± 0.16N |
| Test Solution B | 17.55 | 10.52 ± 0.60N | 18.27 ± 0.14N |
| Test Solution C | 74.01 | 34.63 ± 2.38N | 70.14 ± 0.53N |
| Test Solution D | 9.456 | 5.30 ± 0.07N | 8.19 ± 0.10N |
| Test Solution E | 18.37 | 8.21 ± 0.46N | 13.15 ± 0.09N |
| Test Solution F | 72.30 | 17.35 ± 0.14N | 31.13 ± 0.66N |
| Test Solution G | 269.6 | 34.96 ± 0.75N | 65.01 ± 1.43N |

As the result of this experiment, it was found that the syringe of Example 2 had a lower maximum sliding resistance value than the syringe of Comparative Example 4, whereby an administering operation can be easily performed. As the result of comparing the test solution B with the test solution E and the test solution C with the test solution F which have relatively close values of viscosity, it was found that the maximum sliding resistance value does not depend only on the viscosity but also on the contained ingredient. Specifically, it was confirmed, in the test solutions D to G in which actual drugs (antibody drugs) were used rather than in the dummy solutions of the test solutions A to C, that the syringe of Example 2 had a lower maximum sliding resistance value and a more outstanding effect than the syringe of Comparative Example 4. Since the antibody drug is a kind of protein preparations, it is estimated that the similar effect can be obtained for the protein preparations as well.

A syringe with needle according to the present disclosure is the following syringe.

(1) A syringe with needle including: an outer cylinder including an outer cylinder body part and a needle fixing part provided at a distal end part of the outer cylinder body part; an injection needle having a puncturing needle tip at a distal end, a proximal end part of the injection needle being fixed to the needle fixing part of the outer cylinder; and a gasket housed in the outer cylinder and capable of sliding within the outer cylinder in a liquid-tight state, wherein the injection needle is such a tapered part holding injection needle that a puncturing time piercing part having the puncturing needle tip has an outer diameter of 0.42 mm or less and has a thickness of 0.1 mm or less, the tapered part holding injection needle having a proximal end with a greater outer diameter than the puncturing time piercing part, or the injection needle is such a small diameter ultrathin injection needle that a puncturing time piercing part having the puncturing needle tip has an outer diameter of 0.42 mm or less and has a thickness of 0.04 mm or less, the small diameter ultrathin injection needle extending from a distal end to a proximal end with substantially the same outer diameter, a lubricant is not applied to an inner surface of the outer cylinder, and the gasket can include a gasket body made of an elastic body and a soft coating provided on at least a portion that comes into contact with the inner surface of the outer cylinder, the soft coating having a liquid-tight sliding property with respect to the inner surface of the outer cylinder.

In this syringe with needle, the injection needle is the above-mentioned tapered part holding injection needle or small diameter thin injection needle, the lubricant is not applied to the inner surface of the outer cylinder, and the gasket can include the above-mentioned soft coating having the liquid-tight sliding property with respect to the inner surface of the outer cylinder, whereby a drug solution having a high concentration or a high viscosity can be administered at low injection resistance and with low gasket pressing force, and denaturation of a placed medical liquid due to the lubricant does not occur.

(2) The syringe with needle according to the above-mentioned (1), wherein the syringe with needle is configured such that the gasket within the outer cylinder has an initial sliding resistance value around or equal to or less than a maximum value of a dynamic sliding resistance value.

(3) The syringe with needle according to the above-mentioned (1), wherein an inner surface of the injection needle has an average roughness (Ra) of less than 0.3 μm.

(4) The syringe with needle according to any of the above-mentioned (1) to (3), wherein the tapered part holding injection needle is configured such that the outer diameter of the proximal end is greater than the outer diameter of the puncturing time piercing part by 0.05 mm or more.

(5) The syringe with needle according to any of the above-mentioned (1) to (4), wherein the tapered part holding injection needle can include the puncturing time piercing part extending by a predetermined length with substantially the same outer diameter, and a tapered part expanded in diameter in a tapered manner from a proximal end toward a rear end of the puncturing time piercing part.

(6) The syringe with needle according to any of the above-mentioned (1) to (4), wherein the tapered part holding injection needle can include the puncturing time piercing part extending by a predetermined length with substantially the same outer diameter, a tapered part expanded in diameter in a tapered manner from a proximal end toward a rear end of the puncturing time piercing part, and a proximal end part extending by a predetermined length with substantially the same outer diameter from the tapered part.

(7) The syringe with needle according to any of the above-mentioned (1) to (6), wherein the soft coating is formed by a solidified substance of a soft coating forming liquid substance applied to an outer surface of the gasket body.

(8) The syringe with needle according to any of the above-mentioned (1) to (7), wherein the outer cylinder is made of a synthetic resin.

(9) The syringe with needle according to any of the above-mentioned (1) to (8), wherein the tapered part holding injection needle is fixed to the needle fixing part of the outer cylinder at a proximal end side portion of the tapered part.

(10) The syringe with needle according to any of the above-mentioned (1) to (9), wherein the syringe can include a plunger for pressing the gasket.

A prefilled syringe according to the present disclosure is the following prefilled syringe.

(11) A prefilled syringe including: the syringe with needle according to any of the above-mentioned (1) to (10); a seal cap that seals a distal end part of the injection needle; and a medical liquid with which the syringe is filled.

Since the above-mentioned syringe with needle is used in this prefilled syringe, the above-mentioned effect is obtained.

(12) The prefilled syringe according to the above-mentioned (11), wherein the medical liquid has a viscosity of 10 mPa·s or more.

(13) The prefilled syringe according to the above-mentioned (11) or (12), wherein the medical liquid is a protein preparation.

A medical liquid administration tool according to the present disclosure is the following medical liquid administration tool.

(14) A medical liquid administration tool including: an autoinjector; and the prefilled syringe according to the above-mentioned (11) to (13) mounted in the autoinjector.

Since the above-mentioned syringe with needle is used in this medical liquid administration tool, the above-mentioned effect is obtained.

The detailed description above describes to a syringe with needle, a prefilled syringe, and a medical liquid administration tool suitable for injecting a high-viscosity drug. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe with needle comprising:
an outer cylinder including an outer cylinder body part and a needle fixing part provided at a distal end part of the outer cylinder body part;
an injection needle having a puncturing needle tip at a distal end, a proximal end part of the injection needle configured to be fixed to the needle fixing part of the outer cylinder; and
a gasket configured to be housed in the outer cylinder and capable of sliding within the outer cylinder in a liquid-tight state;
piercing part of the puncturing needle tip having an outer diameter of 0.42 mm or less and a thickness of 0.1 mm or less, and extending by a predetermined length with a same outer diameter;
a tapered part extending from a proximal end of the piercing part in a proximal direction and expanded in diameter in a tapered manner in the proximal direction, the proximal end part extending from a proximal end of the tapered part with a same outer diameter in the proximal direction;
the gasket includes a gasket body made of an elastic body and a coating provided on at least a portion that comes into contact with the inner surface of the outer cylinder, the coating having a liquid-tight sliding property with respect to the inner surface of the outer cylinder; and
the inner diameter of the piercing part is equal to or greater than 0.05 mm, an outer diameter of a proximal end of the tapered part configured to hold the injection needle is greater than the outer diameter of the piercing part by 0.15 mm or more, a length of the proximal end part is 3.0 mm to 12.0 mm, an inner diameter of a proximal end of the proximal end part is equal to or greater than 0.30 mm, and a ratio of the inner diameter of the piercing part to the inner diameter of the proximal end of the proximal end part is 1:1.5 to 1:2.5.

2. The syringe with needle according to claim 1, wherein the syringe with needle is configured such that the gasket within the outer cylinder has an initial sliding resistance value around or equal to or less than a maximum value of a dynamic sliding resistance value.

3. The syringe with needle according to claim 1, wherein an inner surface of the injection needle has an average roughness (Ra) of less than 0.3 µm.

4. The syringe with needle according to claim 1, wherein the injection needle is configured such that the outer diameter of the proximal end is greater than the outer diameter of the piercing part by 0.05 mm or more.

5. The syringe with needle according to claim 1, wherein the coating is formed by a solidified substance of a coating forming liquid substance applied to an outer surface of the gasket body.

6. The syringe with needle according to claim 1, wherein the outer cylinder is made of a synthetic resin.

7. The syringe with needle according to claim 1, wherein the injection needle is configured to be fixed to the needle fixing part of the outer cylinder at a proximal end side portion of the tapered part.

8. The syringe with needle according to claim 1, wherein the syringe includes a plunger configured to press the gasket.

9. The syringe with needle according to claim 1, wherein a lubricant is not applied to an inner surface of the outer cylinder.

10. A prefilled syringe comprising:
a syringe with needle comprising:
an outer cylinder including an outer cylinder body part and a needle fixing part provided at a distal end part of the outer cylinder body part;
an injection needle having a puncturing needle tip at a distal end, a proximal end part of the injection needle configured to be fixed to the needle fixing part of the outer cylinder; and
a gasket configured to be housed in the outer cylinder and capable of sliding within the outer cylinder in a liquid-tight state;
piercing part of the puncturing needle tip having an outer diameter of 0.42 mm or less and a thickness of 0.1 mm or less, and extending by a predetermined length with a same outer diameter;
a tapered part extending from a proximal end of the piercing part in a proximal direction and expanded in diameter in a tapered manner in the proximal direction, the proximal end part extending from a proximal end of the tapered part with a same outer diameter in the proximal direction;
the gasket includes a gasket body made of an elastic body and a coating provided on at least a portion that comes into contact with the inner surface of the outer cylinder, the coating having a liquid-tight sliding property with respect to the inner surface of the outer cylinder;
the inner diameter of the piercing part is equal to or greater than 0.05 mm, an outer diameter of a proximal end of the tapered part configured to hold the injection needle is greater than the outer diameter of the piercing part by 0.15 mm or more, a length of the proximal end part is 3.0 mm to 12.0 mm, an inner diameter of a proximal end of the proximal end part is equal to or greater than 0.30 mm, and a ratio of the inner diameter of the piercing part to the inner diameter of the proximal end of the proximal end part is 1:1.5 to 1:2.5;
a seal cap configured to seal a distal end part of the injection needle; and
a medical liquid with which the syringe is filled.

11. The prefilled syringe according to claim 10, wherein the medical liquid has a viscosity of 10 mPa·s or more.

12. The prefilled syringe according to claim 10, wherein the medical liquid is a protein preparation.

13. The prefilled syringe according to claim 10,
a lubricant is not applied to an inner surface of the outer cylinder.

14. A medical liquid administration tool comprising:
an autoinjector; and
a prefilled syringe configured to be mounted in the autoinjector, the prefilled syringe comprising:
a syringe with needle comprising:
an outer cylinder including an outer cylinder body part and a needle fixing part provided at a distal end part of the outer cylinder body part;
an injection needle having a puncturing needle tip at a distal end, a proximal end part of the injection needle configured to be fixed to the needle fixing part of the outer cylinder; and
a gasket configured to be housed in the outer cylinder and capable of sliding within the outer cylinder in a liquid-tight state;
piercing part of the puncturing needle tip having an outer diameter of 0.42 mm or less and a thickness of 0.1 mm or less, and extending by a predetermined length with a same outer diameter;
a tapered part extending from a proximal end of the piercing part in a proximal direction and expanded in diameter in a tapered manner in the proximal direction, the proximal end part extending from a proximal end of the tapered part with a same outer diameter in the proximal direction;
the gasket includes a gasket body made of an elastic body and a coating provided on at least a portion that comes into contact with the inner surface of the outer cylinder, the coating having a liquid-tight sliding property with respect to the inner surface of the outer cylinder;
the inner diameter of the piercing part is equal to or greater than 0.05 mm, an outer diameter of a proximal end of the tapered part configured to hold the injection needle is greater than the outer diameter of the piercing part by 0.15 mm or more, a length of the proximal end part is 3.0 mm to 12.0mm, an inner diameter of a proximal end of the proximal end part is equal to or greater than 0.30 mm, and a ratio of the inner diameter of the piercing part to the inner diameter of the proximal end of the proximal end part is 1:1.5 to 1:2.5;

a seal cap configured to seal a distal end part of the injection needle; and a medical liquid with which the syringe is filled.

15. The medical liquid administration tool according to claim 14, wherein the medical liquid has a viscosity of 10 mPa·s or more.

16. The medical liquid administration tool according to claim 14, wherein the medical liquid is a protein preparation.

17. The medical liquid administration tool according to claim 14, wherein a lubricant is not applied to an inner surface of the outer cylinder.

18. The syringe with needle according to claim 1, wherein the coating is a composition comprising a reactive silicone-based resin having a terminal silanol group.

19. The syringe with needle according to claim 1, wherein a length of the piercing part is 4.0 mm to 12.0 mm, and a length of the tapered part is 1.0 mm to 10.0 mm.

20. The syringe with needle according to claim 1, wherein the ratio of the inner diameter of the piercing part to the inner diameter of the proximal end of the proximal end part is 1:1.7 to 1:2.3, and a ratio of a distal outer diameter of the injection needle to a proximal end outer diameter of the injection needle is 1:1.2 to 2.0.

* * * * *